United States Patent [19]

Hubele et al.

[11] 4,438,125

[45] Mar. 20, 1984

[54] ARYLAMINE DERIVATIVES AND USE AS MICROBICIDES

[75] Inventors: Adolf Hubele, Magden; Wolfgang Eckhardt, Lörrach; Peter Riebli, Basel, all of Switzerland

[73] Assignee: Ciba-Geigy Corporation, Ardsley, N.Y.

[21] Appl. No.: 417,232

[22] Filed: Sep. 13, 1982

Related U.S. Application Data

[62] Division of Ser. No. 285,652, Jul. 21, 1981, Pat. No. 4,377,587.

[30] Foreign Application Priority Data

Jul. 25, 1980 [CH] Switzerland .......................... 5709/80
Jul. 25, 1980 [CH] Switzerland .......................... 5710/80

[51] Int. Cl.³ ..................... A01N 37/34; C07C 121/78
[52] U.S. Cl. ................................ 424/269; 260/456 A; 260/465 D; 424/285; 424/303; 424/304; 548/262; 549/487
[58] Field of Search ....................... 260/456 A, 465 D; 548/262; 549/487; 424/269, 285, 303, 304

[56] References Cited

U.S. PATENT DOCUMENTS 4,046,911  9/1977  Hubele .................................. 424/285
4,325,966  4/1982  Punja .................................... 424/285

*Primary Examiner*—Richard Raymond
*Attorney, Agent, or Firm*—Frederick H. Rabin

[57] ABSTRACT

The invention relates to novel microbicides of the general formula I

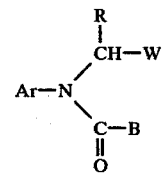

wherein R is hydrogen or methyl, Ar is a phenyl or α-naphthyl group which is substituted by $NH_2$ or $NO_2$ and further radicals, W is a cyano, ester, alkenyl or alkynyl group, and B is alkyl, alkenyl, cyclopropyl, 2-furyl, 2-tetrahydrofuryl, β-(alkoxy)ethyl, triazolylmethyl, methylsulfonylmethyl, alkoxymethyl, alkenyloxymethyl, alkynylmethyl, alkylthiomethyl, alkenylthiomethyl, alkynylthiomethyl, $-OSO_2$-alkyl, $-OSO_2NH$(alkyl) or $-N$(alkyl)$_2$. The invention also describes plant protection compositions which contain these compounds, a process for the production of the novel compounds and compositions, and a method of controlling phytopathogenic microorganisms which comprises the use thereof.

9 Claims, No Drawings

ARYLAMINE DERIVATIVES AND USE AS MICROBICIDES

This is a division of application Ser. No. 285,652 filed on July 21, 1981, now U.S. Pat. No. 4,377,587.

The present invention relates to compounds of the general formula I

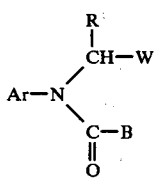

wherein
R is hydrogen or methyl,
Ar is one of the aromatic groups

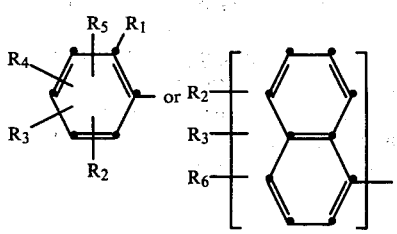

wherein
$R_1$ is $C_1$–$C_3$alkyl, $C_1$–$C_3$alkoxy or halogen,
$R_2$ is $NO_2$ or $NH_2$,
$R_3$ is hydrogen, $C_1$–$C_3$alkyl, $C_1$–$C_3$alkoxy or halogen,
$R_4$ is hydrogen or $C_1$–$C_3$alkyl,
$R_5$ is hydrogen or $C_1$–$C_3$alkyl, and
$R_6$ is hydrogen, $C_1$–$C_3$alkyl or halogen;
W is cyano, $-COOR_8$, $-C(R_9)=C(R_{10})(R_{11})$ or $-C\equiv C-R_{12}$, wherein
$R_8$ is $C_1$–$C_3$alkyl,
$R_9$, $R_{10}$, $R_{11}$ and $R_{12}$, each independently of the other, are hydrogen, $C_1$–$C_3$alkyl or halogen;
B is $C_3$–$C_4$alkyl, $C_2$–$C_4$alkenyl, cyclopropyl, 2-furyl, 2-tetrahydrofuryl, $\beta$-($C_1$–$C_2$-alkoxy)ethyl or the group $CH_2Z$, in which
Z is 1H-1,2,4-triazolyl, methylsulfonyl, $X-R_{13}$, $OSO_2-R_{14}$ or $-N(R_{15})(R_{16})$, in which
X is oxygen or sulfur,
$R_{13}$ is an alkyl, alkenyl or alkynyl group, each containing at most 4 carbon atoms.
$R_{14}$ is $C_1$–$C_3$alkyl or $NH(C_1$–$C_3$alkyl), and
$R_{15}$ and $R_{16}$, each independently of the other, are $C_1$–$C_3$alkyl.

Accordingly, the present invention comprises aniline derivatives whose substituents $R_2$, $R_3$, $R_4$ and $R_5$ in the aniline ring alternate, so that each of these substituents can be in the positions 3, 4, 5 or 6, those compounds being preferred which are disubstituted in both ortho-positions (=2,6 positions). The invention also comprises α-naphthylamine derivatives whose substituents $R_2$, $R_3$ and $R_6$ in the naphthalene ring system alternate, so that each of these substituents can be in the positions 2, 3, 4, 5, 6, 7 or 8, those compounds being preferred which are substituted in the 2-position.

Depending on the indicated number of carbon atoms, alkyl by itself or as moiety of another substituent denotes e.g. the following groups: methyl, ethyl, propyl, or butyl, as well as the isomers thereof, e.g. isopropyl, isobutyl, sec.butyl or tert-butyl. Alkenyl is e.g. vinyl, propen-1-yl, allyl, buten-1-yl, buten-2-yl, buten-3-yl, whilst alkynyl is in particular propargyl. Throughout this specification, the term "halogen" denotes fluorine, chlorine, bromine or iodine, with chlorine or bromine being the preferred identities.

Compounds of the formula I are resins or solids which are stable in air at room temperature and have very valuable microbicidal properties. These compounds are most suitable for controlling harmful microorganisms, in particular for inhibiting or destroying fungi, primarily in agriculture. Particularly preferred compounds are those of the formula I in which the substituent $R_2$ is in the 3-position in the molecule.

Substituted acylaniline derivatives have already been proposed as microbicides, q.v. for example German Offenlegungsschriften Nos. 2 643 477, 2 741 437, 2 513 788, 2 513 732, 2 515 091 or 2 927 461. The known compositions, however, often have numerous drawbacks. These drawbacks include application problems resulting from the physico-chemical properties of the substances and their ability to penetrate or to adhere to the plant which it is desired to protect. In practice, leaf fungicides are usually sprayed onto the plants, forming a microdispersion on the surface thereof. In this state the compositions are necessarily prey to the prevailing weather conditions, such as rain, wind, solar radiation and temperature. Before they can exert their full action, the active ingredients are frequently detached from the body of the plant, for example because of undesirably high water solubility, low light stability, high volatility etc. It is proving exceedingly difficult to find highly effective microbicides which do not exhibit these physico-chemical disadvantages.

There is therefore an urgent need in practice for fungicides which, in very low concentrations, have pronounced fungicidal action and at the same time are capable of adhering to the plant for a sufficient length of time, so as to afford sustained protection against phytopathogenic fungi.

Surprisingly, it has now been found that the novel compounds of the formula I simultaneously possess a number of advantageous properties for the requirements of practice. They have not only a valuable microbicidal spectrum against important harmful fungi, but additional advantages in application. A markedly reduced water solubility and a greatly reduced vapour pressure enable them to exert their fungicidal action more easily and more or less independently of weather conditions, as a much longer contact with the plant is ensured. For this reason the compounds of formula I can be more effectively employed in practice than comparable compounds of the prior art.

Microbicides of the formula I having the following types of substituents or combinations thereof, are preferred:
R: hydrogen, methyl
Ar: substituted phenyl, substituted α-naphthyl,
$R_1$: methyl, ethyl, methoxy, ethoxy, halogen,
$R_2$: $NO_2$, $NH_2$,
$R_3$, $R_6$: hydrogen, methyl, ethyl, methoxy, ethoxy, halogen,
$R_4$, $R_5$: hydrogen, methyl, ethyl,
W: CN, $COOR_8$, $-C(R_9)=C(R_{10})(R_{11})$, $-C\equiv C-R_{12}$,
$R_8$: $C_1$–$C_3$alkyl, $R_9$, $R_{10}$, $R_{11}$, $R_{12}$: hydrogen, methyl, chlorine, bromine, B: $C_3$–$C_{alkyl}$, $C_2$–$C_4$alkenyl, cyclopropyl, 2-furyl, 2-tetrahydrofuryl, $CH_2O(C_1$–$C_3alkyl)$, 1H-1,2,4-triazolylmethyl, $CH_2SO_2CH_3$, $CH_2OSO_2CH_3$, $CH_2OCH_2CH=CH_2$, $CH_2OCH_2C\equiv CH$, $CH_2OSO_2NHCH_3$, $CH_2N(CH_3)_2$, $CH_2N(C_2H_5)_2$, $CH_2N(C_3H_7$—$n)_2$.

A further preferred group of microbicides comprises compounds of the formula I having the following combinations of substitutents:

$R$: methyl,
Ar: substituted phenyl, substituted α-naphthyl,
$R_1$: methyl, methoxy, chlorine, bromine,
$R_2$: $NO_2$, $NH_2$,
$R_3$, $R_6$: hydrogen, methyl, chlorine, bromine,
$R_4$, $R_5$: hydrogen, methyl,
W: CN, $COOR_8$, —$C(R_9)=C(R_{10})(R_{11})$, —C≡C—$R_{12}$,
$R_8$: $C_1$–$C_3$alkyl,
$R_9$, $R_{10}$, $R_{11}$, $R_{12}$: hydrogen, methyl, chlorine,
B: 2-furyl, 2-tetrahydrofuryl, $CH_2O(C_1$–$C_3alkyl)$, 1H-1,2,4-triazolylmethyl, $CH_2SO_2CH_3$, $CH_2OSO_2CH_3$, $CH_2OCH_2CH=CH_2$, $CH_2OCH_2C\equiv CH$, $CH_2OSO_2NHCH_3$, $CH_2N(CH_3)_2$, $CH_2N(C_2H_5)_2$, $CH_2N(C_3H_7$—$n)_2$.

The aniline derivatives within the scope of formula I are particularly preferred and form e.g. the following preferred subgroup of compounds having the following types of substituents or combinations thereof:

$R_1$: halogen, methoxy, methyl,
$R_2$: $NO_2$, $NH_2$,
$R_3$: hydrogen, methoxy, methyl, halogen,
$R_4$, $R_5$, R: hydrogen, methyl,
$R_8$: $C_1$–$C_3$alkyl,
B: 2-furyl, 2-tetrahydrofuryl, $CH_2O(C_1$–$C_3)alkyl$, $CH_2CH_2OCH_3$, 1H-1,2,4-triazolylmethyl, $CH_2SO_2CH_3$, $CH_2OSO_2CH_3$, $CH_2OCH_2CH=CH_2$, $CH_2OSO_2NHCH_3$, $CH_2OCH_2C\equiv CH$.

A preferred group of microbicides comprises aniline derivatives of the formula I having the following combinations of substituents:

$R_1$: methyl,
$R_2$: $NO_2$, $NH_2$,
$R_3$: hydrogen, methyl, methoxy, chlorine, bromine,
$R_4$, $R_5$, R: hydrogen, methyl,
$R_8$: methyl, isopropyl,
B: 2-furyl, 2-tetrahydrofuryl, $CH_2O(C_1$–$C_3alkyl)$, $CH_2CH_2OCH_3$, 1H-1,2,4-triazolylmethyl, $CH_2SO_2CH_3$, $CH_2OSO_2CH_3$, $CH_2OCH_2CH=CH_2$, $CH_2OSO_2NHCH_3$, $CH_2OCH_3C\equiv CH$.

A further preferred group of aniline derivatives of the formula I is characterised by the following combinations of substituents:

$R_1$: chlorine, methoxy,
$R_2$: $NO_2$, $NH_2$,
$R_3$: hydrogen, methyl, methoxy, chlorine, bromine,
$R_4$, $R_5$, R: hydrogen, methyl,
$R_8$: methyl, isopropyl,
B: 2-furyl, 2-tetrahydrofuryl, $CH_2O(C_1$–$C_3alkyl)$, $CH_2CH_2OCH_3$, 1H-1,2,4-triazolylmethyl, $CH_3SO_2CH_3$, $CH_2OSO_2CH_3$, $CH_2OCH_2CH=CH_2$, $CH_2OSO_2NHCH_3$, $CH_2OCH_2C\equiv CH$.

Compounds within the scope of formula I, wherein X is oxygen and $R_{13}$ is a $C_1$–$C_3$alkyl group, are especially preferred, and in particular those in which $R_{13}$ is methyl, ethyl or isopropyl.

Preferred α-naphthylamine derivatives within the scope of formula I are those compounds having the following types or combinations of substituents:

$R_2$: $NO_2$, $NH_2$,
$R_3$: hydrogen, methoxy, methyl, halogen,
$R_6$: hydrogen, methyl, halogen,
R: methyl, hydrogen,
$R_8$: $C_1$–$C_3$alkyl,
B: 2-furyl, 2-tetrahydrofuryl, $CH_2O(C_1$–$C_3alkyl)$, 1H-1,2,4-triazolylmethyl, $CH_2SO_2CH_3$, $CH_2OSO_2CH_3$, $CH_2OCH_2CH=CH_2$, $CH_2OCH_2C\equiv CH$, $CH_2OSO_2NHCH_3$.

A preferred group of microbicides comprises α-naphthylamine derivatives of the formula I having the following combinations of substituents:

$R_2$: $NO_2$, $NH_2$,
$R_3$: hydrogen, methyl, methoxy, chlorine, bromine,
$R_6$: hydrogen, methyl, chlorine, bromine,
R: methyl,
$R_8$: methyl, isopropyl,
B: 2-furyl, 2-tetrahydrofuryl, $CH_2O(C_1$–$C_3alkyl)$, $CH_2CH_2OCH_3$, 1H-1,2,4-triazolylmethyl, $CH_2SO_2CH_3$, $CH_2OSO_2CH_3$, $CH_2OCH_2CH=CH_2$, $CH_2OCH_2C\equiv CH$, $CH_2OSO_2NHCH_3$.

A further preferred group of α-napthylamine derivatives of the formula I is characterised by the following combinations of substituents:

$R_2$: $NO_2$, $NH_2$,
$R_3$: hydrogen, methyl,
$R_6$: hydrogen, methyl,
R: methyl,
$R_8$ methyl, isopropyl,
B: 2-furyl, 2-tetrahydrofuryl, $CH_2O(C_1$–$C_3alkyl)$, $CH_2CH_2OCH_3$, 1H-1,2,4-triazolylmethyl, $CH_2SO_2CH_3$, $CH_2OSO_2CH_3$, $CH_2OCH_2CH=CH_2$, $CH_2OCH_2C\equiv CH$, $CH_2OSO_2NHCH_3$.

A group of particularly preferred microbicides comprises compounds of the formula I, wherein Ar is the group

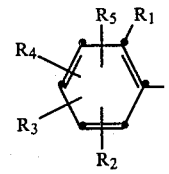

$R_1$ is $C_1$–$C_3$alkyl, $C_1$–$C_3$alkoxy or halogen,
$R_2$ is $NO_2$ $NH_2$,
$R_3$ is hydrogen, $C_1$–$C_3$alkyl, $C_1$–$C_3$alkoxy or halogen,
$R_4$ is hydrogen or $C_1$–$C_3$alkyl,
$R_5$ is hydrogen or $C_1$–$C_3$alkyl, with the proviso that both ortho-positions in the aniline part of the molecule are always substituted,
R is hydrogen or methyl,
W is $COOR_8$,
$R_8$ is $C_1$–$C_3$alkyl,
B is 2-furyl, 2-tetrahydrofuryl, β-($C_1$–$C_2$alkoxy)ethyl or the group $CH_2Z$, in which Z is 1H-1,2,4-triazolyl, methylsulfonyl, X—$R_{13}$ or $OSO_2$—$R_{14}$, wherein X is oxygen or sulfur, $R_{13}$ is an alkyl, alkenyl or alkynyl group, each of which contains at most 4 carbon atoms, and $R_{14}$ is $C_1$–$C_3$alkyl or $NH(C_1$–$C_3alkyl)$.

A further particularly preferred group of microbicides comprises compounds of the formula I, wherein Ar is the group

[Naphthalene ring structure with substituents]
R$_2$—
R$_3$—
R$_6$—

R$_2$ is NO$_2$ or NH$_2$,

R$_3$ is hydrogen, C$_1$–C$_3$alkyl, C$_1$–C$_3$alkoxy or halogen,

R$_6$ is hydrogen, C$_1$–C$_3$alkyl or halogen, with the proviso that the β-position in the molecule is always substituted, W is COOR$_8$, R$_8$ is C$_1$–C$_3$alkyl, B is 2-furyl, 2-tetrahydrofuryl, β-(C$_1$–C$_2$alkoxy)ethyl or the group CH$_2$Z, in which Z is 1H-1,2,4-triazolyl, sulfonylmethyl, X—R$_{13}$ or OSO$_2$—R$_{14}$, wherein X is oxygen or sulfur, R$_{13}$ is an alkyl, alkenyl or alkynyl group, each containing at most 4 carbon atoms, and R$_{14}$ is C$_1$–C$_3$alkyl or NH(C$_1$–C$_3$alkyl).

The following individual compounds are particularly preferred on account of their pronounced action against phytopathogenic microorganisms:

N-(1′-methoxycarbonylethyl)-N-methoxyacetyl-2-methyl-6-aminoaniline,

N-(1′-methoxycarbonylethyl)-N-methoxyacetyl-2-methyl-6-nitroaniline,

N-(1′-methoxycarbonylethyl)-N-methoxyacetyl-2,6-dimethyl-3-nitroaniline,

N-(1′-methoxycarbonylethyl)-N-ethoxyacetyl-2,6-dimethyl-3-nitroaniline,

N-(1′-isopropyloxycarbonylethyl)-N-methoxyacetyl-2,6-dimethyl-3-nitroaniline,

N-(1′methoxycarbonylethyl)-N-methoxyacetyl-2,6-dimethyl-3-aminoaniline,

N-(1′methoxycarbonylethyl)-N-methoxyacetyl-2,3-dimethyl-6-aminoaniline,

N-(1′methoxycarbonylethyl)-N-methoxyacetyl-2,3-dimethyl-6-nitroaniline,

N-(1′methoxycarbonylethyl)-N-(2-furyl)-2-methyl-6-nitroaniline,

N-(1′-methoxycarbonylethyl)-N-(2-tetrahydrofuryl)-2-methyl-6-nitroaniline.

1N-(1′-methoxycarbonylethyl)-1N-methoxyacetyl-1,2-diaminonaphthalene,

N-(1′-methoxycarbonylethyl)-N-methoxyacetylamino-2-nitronaphthalene,

N-(1′-methoxycarbonylethyl)-N-methoxyacetylamino-2-methyl-3-nitronaphthalene,

N-(1′methoxycarbonylethyl)-N-ethoxyacetylamino-2-ethyl-3-nitronaphthalene,

N-(1′-isopropyloxycarbonylethyl)-N-methoxyacetylamino-2-methyl-3-nitronaphthalene, 1N-(1′-methoxycarbonylethyl)-1N-methoxyacetyl-2-methyl-1,3-diaminonaphthalene, 1N-(1′-methoxycarbonylethyl)-1N-methoxyacetyl-3-methyl-1,2-diaminonaphthalene, N-(1′-methoxycarbonylethyl)-N-methoxyacetyl-amino-3-methyl-2-nitronaphthalene, N-(1′-methoxycarbonylethyl)-N-(2-furyl)amino-2-nitronaphthalene and N-(1′-methoxycarbonylethyl)-N-(2-tetrahydrofuryl)amino-2-nitronaphthalene.

Depending on the nature of the substitution, the compounds of formula I can be obtained by a variety of methods, as set forth under A to J below. In the formulae Ia, Ib, Ia′, Ib′, and II to XVIII, the substituents R$_1$ to R$_{16}$, X, B, W and Ar are as defined for formula I. Y is a customary leaving group, e.g. benzenesulfonyloxy, p-bromobenzenesulfonyloxxy, p-tosyloxy, trifluoroacetyloxy, lower alkylsulfonyloxy such as mesyloxy or, in particular, halogen such as fluorine, chlorine, bromine or iodine. Hal denotes fluorine, chlorine, bromine or iodine, especially chlorine or bromine.

The individual procedures to be followed in the process of the invention may be set forth as follows:

A. Compounds of the formula I can be prepared by acylating a compound of the formula II $$\text{Ar—N} \begin{array}{c} \text{CH—W} \\ | \\ \text{R} \\ \text{H} \end{array} + \text{B—COOH} \xrightarrow{\text{acylation}} \text{(I)}$$

(II)  (III)

with a carboxylic acid of the formula III or a reactive derivative thereof, or

B. by reacting a compound of the formula IV $$\text{Ar—N} \begin{array}{c} \text{H} \\ \text{CO—B} \end{array} + \text{Y—CH—W} \xrightarrow{-\text{HY}} \text{(I)}$$

(IV)  (V)

with a compound of the formula V, wherein Y is a customary leaving group, or

C. by nitrating a compound of the formula VI or VI′

[Structure VI with substituents R$_4$, R$_5$, R$_3$, R$_1$, R, CH—W, N, CO—B]

(VI)

[Structure Ia with substituents R$_4$, R$_5$, R$_3$, R$_1$, R, CH—W, N, CO—B, NO$_2$]

(Ia)

nitration (NO$_2^+$)

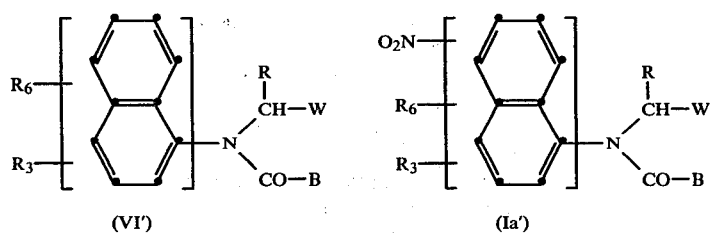

with a reactive nitrating reagent to give a compound of the formula I, which is here and subsequently referred to as Ia or Ia', or D. by hydrogenating a compound of the subgroup Ia or Ia'

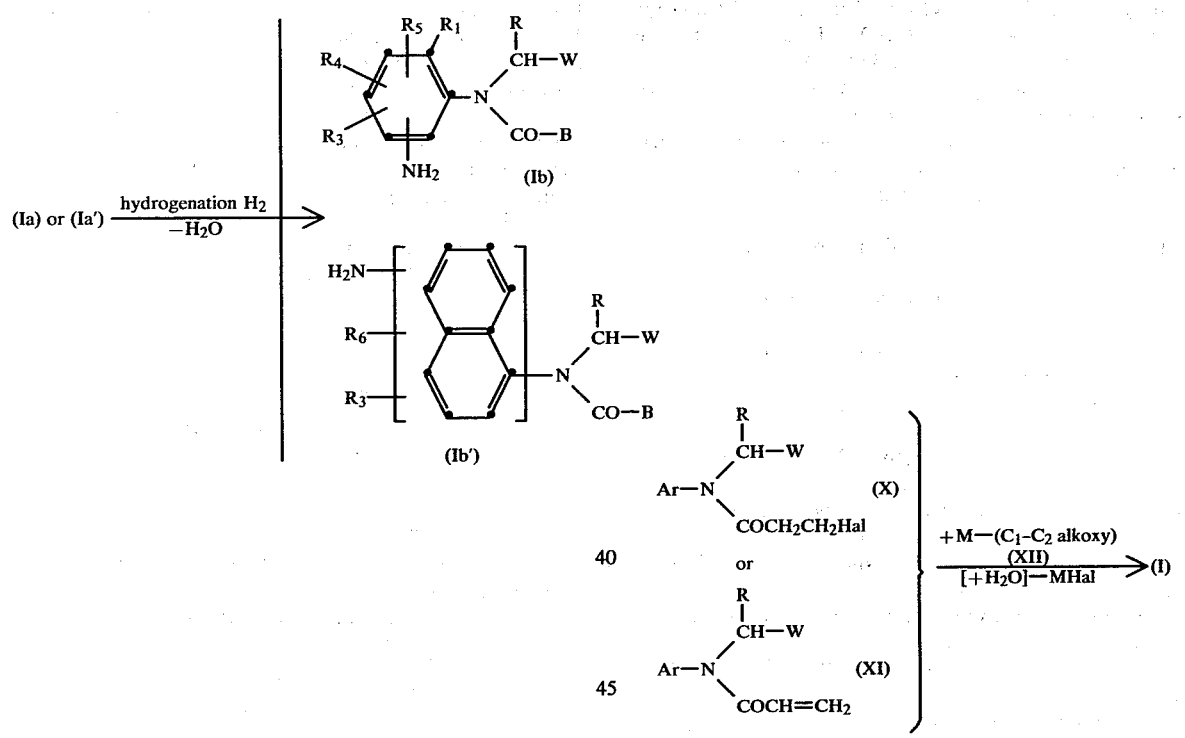

with a conventional hydrogenating agent to give a compound of the formula I, which is here and subsequently referred to as Ib or Ib', or E. where B in compounds of the formula I is the $CH_2XR_{13}$ group or a 1H-1,2,4-triazolylmethyl group, by reacting a compound of the formula VII

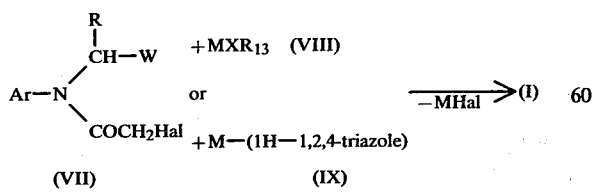

with a compound of the formula VIII or IX, or

F. where B in compounds of the formula I is 4-($C_1$-$C_2$alkoxy)ethyl, by reacting a compound of the formula X or XI with a compound of the formula XII, the reaction of XI with XII initially producing an adduct which can be converted by hydrolysis into the final product of formula I, or G. by esterifying or transesterifying a compound of the formula XIII

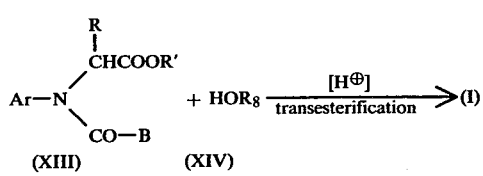

in the presence of a strong acid, with a compound of the formula XIV, wherein R' is hydrogen or a hydrocarbon radical, or H. where Z in the compounds of formula I is methylsulfonyl, by reacting a compound of the formula VII with a compound of the formula XV

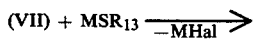

(XV)

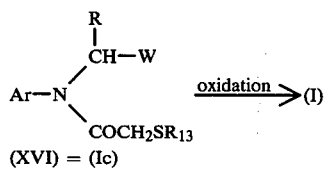

(XVI) = (Ic)

to give an intermediate of the formula XVI and then oxidising XVI to I, the compounds of formula XVI being designated as subgroup Ic, or J. where B in compounds of the formula I is $CH_2OSO_2R_{14}$, by reacting a compound of the formula XVII

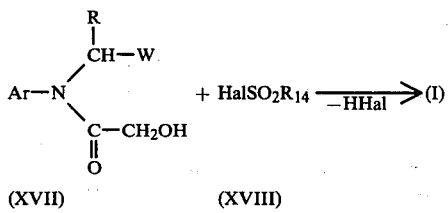

(XVII)            (XVIII)

with a compound of the formula XVIII. In the above process variants A to J, the substituents $R_1$ to $R_{16}$, X, W, B and Ar in formulae Ia, Ib, Ia', Ib' and II to XVIII are as defined for formula I, M is hydrogen or a metal cation and Hal is a halogen atom.

Most of the starting materials are known or they can be obtained by methods which are known per se. The starting compounds of the formulae II, IV, VII, X, XI and XII can be prepared e.g. by methods similar to those described in process variants C and D by nitration of the aniline derivatives and, if desired, subsequent hydrogenation thereof.

It is advantageous to carry out the process variants under the following reaction conditions:

Variant A: In this variant a reactive derivative of a compound of the formula III, e.g. the acid halide, acid anhydride or the ester, can conveniently be used. The acid chloride and bromide are particularly suitable.

The reaction temperatures are in the range from 0° to 180° C., with the preferred range being from 0° to 150° C. or the boiling point of the solvent or mixture of solvents. In some cases it is advantageous to use acid acceptors or condensation agents, such as organic and inorganic bases, e.g. tertiary amines such as trialkylamines (trimethylamine, triethylamine, tripropylamine etc.), pyridine and pyridine bases (4-dimethylaminopyridine, 4-pyrrolidyl-aminopyridine etc.), oxides and hydroxides, carbonates and bicarbonates of alkali metals and alkaline earth metals, as well as alkali acetates.

The hydrogen halide formed can also in some cases be expelled from the reaction mixture by introducing an inert gas, e.g. nitrogen. The N-acylation can be carried out in the presence of inert solvents or diluents, for example aliphatic and aromatic hydrocarbons such as benzene, toluene, xylenes, petroleum ether; halogenated hydrocarbons such as chlorobenzene, methylene chloride, ethylene chloride, chloroform, carbon tetrachloride, tetrachloroethylene; ethers and ethereal compounds such as dialkyl ethers (diethyl ether, diisopropyl ether, tert-butylmethyl ether etc.), anisole, dioxane, tetrahydrofurane; nitriles such as acetonitrile, propionitrile; N,N-dialkylated amides such as dimethyl formamide; dimethyl sulfoxide; ketones such as acetone, diethyl ketone, methyl ethyl ketone; and mixtures of such solvents with each other. In some cases the acylating agents itself can be employed as solvent. The presence of a reaction catalyst, such as dimethyl formamide, ca be advantageous in the acylation.

Variant B: In this variant the substituent Y in formula V is a customary leaving group, for example benzenesulfonyloxy, p-bromobenzenesulfonyloxy, p-tosyloxy, trifluoroacetyloxy, lower alkylsulfonyloxy such as mesyloxy, or especially a halogen such as fluorine, chlorine, bromine or iodine, preferably chlorine or bromine. In this variant it is convenient to convert the starting compound of the formula VI first with butyl lithium, sodium hydride or an alkali carbonate (e.g. sodium carbonate) into the corresponding alkali salt, or else the process is carried out in the presence of an acid acceptor in the same temperature range as in variant A, preferably with the addition of catalytic amounts of alkali iodide.

Variant C: Suitable nitrating agents for this variant are all substances which are able to liberate the actual nitrating reagent, viz. the nitronium ion $NO_2^+$. Hence in addition to nitric acid and nitrating acid ($1HNO_3:2 H_2SO_4$) it is also possible to use organic nitrates such as acyl nitrates (e.g. acetyl nitrate) in their convenient formulation (e.g. mixture of glacial acetic acid/acetic anhydride/65-100% $HNO_3$) as nitrating agent. To increase the reaction rate the reaction mixture can also be warmed, but the temperature should not be raised so sharply that nitrous gases are formed.

Variant D: For the hydrogenation of the nitro group it is possible to use, in particular, lower alkanols such as methanol, ethanol, or isopropanol, in addition to the conventional inert organic solvents. Suitable solvents are also aliphatic and aromatic hydrocarbons such as benzene, toluene, xylenes, petroleum ether; ethers and ethereal compounds such as dialkyl ethers (diisopropyl ether, tert-butylmethyl ether etc.), anisole, dioxane, tetrahydrofurane; dimethyl sulfoxide; or esters such as ethyl acetate, propyl acetate etc.

Whenever the starting material of the formula Ia or Ia' is liquid, hydrogenation can also be effected without a solvent. In addition, it is also possible to carry out the hydrogenation in multiphase systems, e.g. in toluene/$H_2O$ or xylene/$H_2O$, and also in glacial acetic acid.

The hydrogenation can be carried out in widely different manner. In addition to conventional methods with nascent hydrogen (base metals in acid solution), electrolysis, or with reducing agents such as alkali hydrides or lithium aluminium hydride, catalytic methods of hydrogenation are particularly suitable.

Suitable hydrogen catalysts are black catalysts (very finely divided metal precipitates, e.g. metals or noble metals precipitated from solutions of their salts by reduction) such as platinum, palladium or nickel: noble metal oxides such as platinum (IV) oxide; skeleton catalysts consisting of suspensions of binary allys, e.g. raney nickel; carrier catalysts consisting of black catalysts which adhere to the surface of a carrier substance such as charcoal, silica, alumina, sulfates and carbonates of alkaline earth metals; oxide and sulfide catalysts such as copper chromite, zinc chromite, molybdenum sulfide, tungsten sulfide etc.

The hydrogenation is preferably carried out under normal pressure or at pressures up to 20 bar, while the reaction temperatures are in the range from 0° to 150° C. If catalysts other than those specified above are employed, e.g. iron, chromium, cobalt or copper, then higher reaction temperatures and higher pressures are required for the hydrogenation.

Variant E: When M is hydrogen it is advantageous to use a salt-forming agent, e.g. an oxide, hydroxide or hydride of an alkali metal or alkaline earth metal.

Variant F: For the reaction of $(X)+(XII)\rightarrow(I)$, the same procedure as in Variant E is followed.

The reaction of $(XI)+(XII)\rightarrow(I)$ is carried out with the alcohol or the alcoholate $XII(M=a$ metal atom) as a Michael addition reaction.

Variant G: This reaction is catalytically influenced by acids and bases. In order to shift the quilibrium in the desired direction, the process is carried out with an excess of $HOR_8.R'$ and $R_8$ have different meanings. $R'$ is hydrogen or a hydrocarbon radical, and is in particular hydrogen or lower alkyl, such as methyl or ethyl.

Variant H: The reaction of $(VII)+(XV)\rightarrow(XVI)$ is carried out by the same procedure as in variant E. The oxidation of $(XVI)$ to $(I)$ can the carried out with peracids such as $H_2O_2$, perbenzoic acid, metachloroperbenzoic acid, $HIO_4$ or also potassium permanganate. Preferred oxidants are peracids, especially $H_2O_2$.

Variant J: The reaction is carried out by the same procedure as in variant E, but the compound of the formula XVII can also first be converted into the corresponding alcoholate and then reacted with the compound XVIII.

In all process variants it can be advantageous to use anhydrous organic solvents and/or organic solvents which are saturated with inert gases. Carrying out the process in an inert gas atmosphere, e.g. under $N_2$, can also advantageously influence the reaction course.

Where no specific solvents are mentioned in process variants A to J, it is, in principle, possible to employ all solvents which are inert to the reactants. Examples of such solvents are: aliphatic and aromatic hydrocarbons such as benzene, toluene, xylenes, petroleum ether, halogenated hydrocarbons such as chlorobenzene, methylene chloride, ethylene chloride, chloroform; ethers and ethereal compounds such as dialkyl ethers, dioxane, tetrahydrofurane; nitriles such as acetonitrile; N,N-dialkylated amides such as dimethyl formamide; dimethyl sulfoxide; ketones such as methyl ethyl ketone; and mixtures of such solvents with each other. In the described process it is not as a rule necessary to isolate the intermediate. The process can also be carried out continuously in the same reaction vessel.

The process for obtaining the compounds of formula I, including all the partial steps (variants A to J), also constitutes an object of the invention.

Where the substituent R in the compounds of formula I is methyl, these compounds have an asymmetrical carbon atom in the side chain adjacent to W and can be resolved into their optical antipodes in conventional manner. Thus, for example, by fractional crystallisation of the salts of II with an optically active acid and further reaction of the optically pure compounds of II to I, or by fractional crystallisation of the free acid XIII $(R'=H)$ with an optically active base and further reaction of the optically pure compounds of XIII to I. The optical antipodes of I possess different microbicidal properties.

Depending on the substitution, further asymmetrical carbon atoms can be present in the molecule.

Irrespective of the cited optical isomerism, an atropisomerism is observed at the phenyl $-1N<$ axis when the phenyl ring is substituted unsymmetrically to this axis.

Provided no synthesis with the object of isolating pure isomers is carried out, a compound of the formula I will normally be obtained as a mixture of these possible isomers.

Surprisingly, it has been found that compounds of the formula I possess, for practical purposes, a very useful microbicidal spectrum. They can be used, for example, for protecting cultivated plants.

The principal field of use of compounds of the formula I resides in the control of harmful microorganisms, especially phytopathogenic fungi. Accordingly, these compounds have a very useful curative and preventive action for protecting cultivated plants without adversely affecting these by undesirable side-effects. Examples of cultivated plants within the scope of this invention are: cereals (wheat, barley, rye, oats, rice) beet (sugar beet and fodder beet), drupes, pomes and soft fruit (apples, pears, plums, peaches, almonds, cherries, strawberries, raspberries and blackberries), leguminous plants (beans, lentils, peas, soybeans), oil plants (rape, mustard, poppy, olives, sunflowers, coconuts, castor oil plants, cocoa beans, ground nuts), cucumber plants (cucumber, marrows, melons), fibre plants (cotton, flax, hemp, jute), citrus fruit (oranges, lemons, grapefruit, mandarins), vegetables (spinach, lettuce, asparagus, cabbages, carrots, onions, tomatoes, potatoes, paprika), or plants such as maize, tobacco, nuts, coffee, sugar cane, tea, vines, hops, bananas and natural rubber plants, as well as ornamentals.

With the compounds of the formula I it is possible to inhibit or destroy the microorganisms which occur in plants or parts of plants (fruit, blossoms, leaves, stems, tubers, roots) in these and also related crops of useful plants, and also to protect from attack by such microorganisms the parts of plants which grow later. The compounds of formula I are effective against the following phytopathogenic fungi; against the Oomycetes belonging to the class of the Phycomycetes, such as Peronosporales (Phytophthora, Pythium, Plasmopara), and also against Ascomycetes such as Erysiphe and Venturia pathogens.

The compounds of the formula I furthermore have a systemic action and can also be used as seed dressing agents for protecting seeds (fruit, tubers, grains) and plant cuttings from fungus infections and from microorganisms which occur in the soil.

Accordingly, the invention also relates to the use of compounds of the formula I for controlling phythopathogenic microorganisms and for the preventive treatment of plants to protect them from attack by such microorganisms.

The compounds of the formula I can be applied to the area or plant to be treated, simultaneously or in succession, with further compounds. These compounds can be both fertilisers or micronutrient donors or other preparations that influence plant growth. They can also be selective herbicides, insecticides, fungicides, bactericides, nematicides, molluscicides or mixtures of several of these preparations, if desired together with further carriers, surfactants or application-promoting adjuvants customarily employed in the art of formulation. Suitable carriers and adjuvants can be solid or liquid and correspond to the substances ordinarily employed in formulation technology, e.g. natural or regenerated mineral substances solvents, dispersants, wetting agents, tackifiers, binders or fertilisers.

Surfactants shall be understood as meaning here surface-active compounds which are usually dissolved or dispersed in a liquid and are preferably adsorbed at interfaces. A surfactant molecule contains at least one group having affinity for substances of strong polarity—thereby generally causing solubility in water——and at least one further group having weak affinity for water. Surfactants are therefore molecules containing a hydrophobic (i.e. lipophilic) component, usually a hydrocarbon radical containing alkyl or aryl moieties, and a hydrophilic (i.e. lipophobic) component, e.g. a perfluoroalkyl radical. The products used in actual practice are usually mixtures of these compounds. Surfactants permit not only a dispersion of the active ingredient in a liquid, e.g. aqueous, medium, but also an increased wettability of the plants, which results in a reduction of the amount of active ingredient in the ready-for-use composition and consequently in a lesser environmental impact.

The content of active ingredient in commercial compositions is from 0.01% to 90% by weight and that of adjuvants is 10 to 99.99% by weight, these latter generally comprising 0 to 30% by weight of a surfactant.

The invention also relates to compositions which contain a compound of the formula I as at least one active ingredient, and to the use of such compositions for controlling and/or preventing attack by microorganisms. In addition, the invention also relates to the preparation of said compositions, which comprises homogeneously mixing the active ingredient with one or more substances or groups of substances as described herein. The invention further relates to a method of conrolling microorganisms, which comprises applying the compounds of the formula I or compositions containing them.

The following Examples will serve to illustrate the invention in more detail, without implying any restriction to what is described therein. Parts and percentages are by weight. Unless otherwise stated, a compound of the formula I will always be understood as meaning the mixture of isomers.

EXAMPLE 1

Preparation of

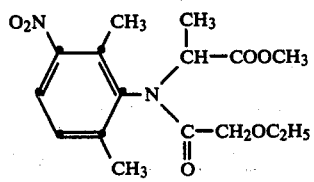

(31)

N-(1'-methoxycarbonylethyl)-N-ethoxyacetyl-2,6-dimethyl-3-nitroaniline

To a solution of 3 g of 55% sodium hydride in 70 ml of anhydrous tetrahydrofurane saturated with nitrogen is added dropwise, at room temperature, with stirring and while simultaneously introducing nitrogen, a solution of 16 g N-ethoxyacetyl-2,6-dimethyl-3-nitroaniline in 30 ml of the same solvent. After the weakly exothermic reaction has subsided, the mixture is heated to 55° C. and 12.7 g of methyl 2-bromopropionate in 20 ml of tetrahydrofurane are added. During this addition the temperature rises to 60° C. The mixture is stirred for 12 hours at 55° C., then cooled to room temperature, poured into 100 ml of water and extracted with two 100 ml portions of ethyl acetate. The combined extracts are washed with water, dried over sodium sulfate, and excess solvent is removed in vacuo. The oily crude product is purified by column chromatography over silica gel, using a 1:1 mixture of chloroform/diethyl ether as eluant. Fractions 5 to 30 are combined and the eluant is removed in vacuo. Compound 31 is a viscous oil with a refractive index of $n_D^{24}=1.5325$.

EXAMPLE 2

Preparation of

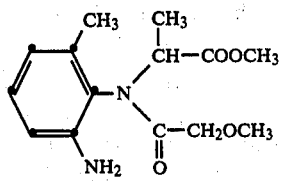

(2)

N-(1'-methoxycarbonylethyl)-N-methoxyacetyl-2-amino-6-methyl-aniline 257.4 g of N-(1'-methoxycarbonylethyl)-N-methoxyacetyl-2-methyl-6-nitroaniline are dissolved in 2.6 liters of anhydrous methanol and the solution is hydrogenated for 26 hours at 20°-25° C. and under normal pressure in the presence of 26 g of raney nickel (uptake of $H_2$: 56.2 liters=100% of theory). The catalyst is then removed by filtration, the filtrate is concentrated, and the oily residue is crystallised by adding diethyl ether. Yield: 170.8 g of compound 2 with a melting point of 86°-88° C.

EXAMPLE 3

Preparation of

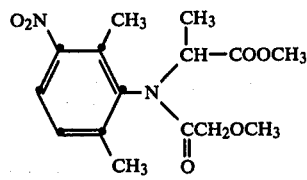

(28)

N-(1'-methoxycarbonylethyl)-N-methoxyacetyl-2,6-dimethyl-3-nitroaniline 15.2 g of methoxyacetyl chloride are added dropwise at room temperature to 32 g of N-(1'methoxycarbonylethyl)-2,6-dimethyl-3-nitroaniline.

After the weakly exothermic reaction has subsided, the reaction solution is stirred for 20 hours at room temperature. The solvent is then removed and the dark red oily residue is distilled in a high vacuum. Compound 28 distills at a temperature of 170°-174° C. and a pressure of 0.07 mbar as a pale yellow oil.

EXAMPLE 4

Preparation of

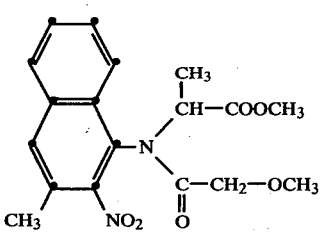
(402)

N-1′-methoxycarbonylethyl)-N-methoxyacetylamino-3-methyl-nitronaphthalene

To a solution of 3 g of 55% sodium hydride in 70 ml of anhydrous tetrahydrofurane saturated with nitrogen is added dropwise, at room temperature, with stirring and while simultaneously introducing nitrogen, a solution of 14 g of N-methoxyacetylamino-3-methyl-2-nitronaphthalene in 30 ml of the same solvent. After the weakly exothermic reaction has subsided, the mixture is heated to 55° C. and 9.5 g of methyl 2-bromopropionate in 20 ml of tetrahydrofurane are added. During this addition the temperature rises to 60° C. The mixture is stirred for 12 hours at 55° C., then cooled to room temperature, poured into 100 ml of water and extracted with two 100 ml portions of ethyl acetate. The combined extracts are washed with water, dried over sodium sulfate, and excess solvent is removed in vacuo. The oily crude product is purified by column chromatography over silica gel, using a 1:1 mixture of chloroform/diethyl ether as eluant. Fractions 5 to 30 are combined and the eluant is removed in vacuo. Compound 402 is obtained as a viscous resin.

EXAMPLE 5

Preparation of

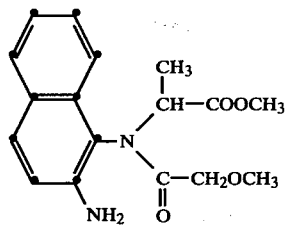
(701)

1-N-(1′-methoxycarbonylethyl)-1N-methoxycarbonyl-1,2-diaminonaphthalene 3 g of N-(1′methoxycarbonylethyl)-N-methoxyacetylamino-2-nitronaphthalene are dissolved in 100 ml of dioxane and the solution is hydrogenated for 26 hours at 20°–25° C. under normal pressure in the presence of 4 g of raney nickel (uptake of $H_2$: 590 ml=approx. 100% of theory). The catalyst is then removed by filtration, the filtrate is concentrated and the residue is digested with a small amount of petroleum ether. Yield: 2 g. Melting point: 159°–162° C.

EXAMPLE 6

Preparation of

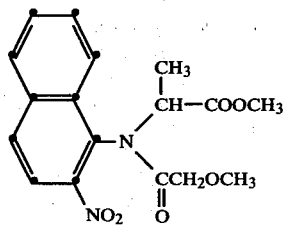
(400)

N-(1′methoxycarbonylethyl)-N-methoxyacetyl-2-nitronaphthylamine

With stirring, 7.2 g of N-methoxyacetyl-2-nitronaphthylamine in 50 ml of anhydrous tetrahydrofurane are added dropwise at room temperature to 0.8 g of 80% sodium hydride in 70 ml of the same solvent. After the weakly exothermic reaction has subsided, the clear solution is stirred for 1 hour at room temperature and then 4.8 g of methyl 2-bromopropionate in 20 ml of tetrahydrofurane are added. Stirring is continued for 20 hours at 50° C., then the suspension is cooled to room temperature and poured into 200 ml. of water. After extraction with two 100 ml portions of diethyl ether, the combined extracts are washed with water, dried over sodium sulfate, and excess solvent is removed in vacuo. The oily crude product is chromatographed over a column of silica gel with a 1:1 mixture of chloroform/diethyl ether as eluant. Fractions 11 to 26 are combined and the eluant is removed in vacuo. Compound 400 is obtained in the form of yellow crystals which melt at 103°–107° C.

The following compounds of formula I are prepared in similar manner:

TABLE 1

| | Compounds of formula I in which Ar = substituted phenyl, W = $COOR_8$, $R_5$ =H | | | | | | | |
|---|---|---|---|---|---|---|---|---|
| Compound | $R_1$ | $R_2$ | $R_3$ | $R_4$ | R | $R_8$ | B | Physical data [°C.] |
| 1 | $CH_3$ | 6-$NH_2$ | H | H | H | $CH_3$ | $CH_2OCH_3$ | |
| 2 | $CH_3$ | 6-$NH_2$ | H | H | $CH_3$ | $CH_3$ | $CH_2OCH_3$ | m.p. 103–109 |
| 3 | $C_2H_5$ | 6-$NH_2$ | H | H | H | $CH_3$ | $CH_2OCH_3$ | |
| 4 | $CH_3$ | 6-$NH_2$ | H | H | $CH_3$ | $C_2H_5$ | $CH_2OCH_3$ | |
| 5 | $CH_3$ | 6-$NH_2$ | H | H | $CH_3$ | $C_3H_7$—i | $CH_2OCH_3$ | |
| 6 | Cl | 6-$NH_2$ | H | H | $CH_3$ | $CH_3$ | $CH_2OCH_3$ | m.p. 103–105 |
| 7 | $CH_3$ | 6-$NH_2$ | 3-$CH_3$ | H | H | $CH_3$ | $CH_2OCH_3$ | |
| 8 | $CH_3$ | 6-$NH_2$ | 3-$CH_3$ | H | $CH_3$ | $CH_3$ | $CH_2OCH_3$ | m.p. 158–164 |
| 9 | $CH_3$ | 3-$NH_2$ | H | 6-$CH_3$ | H | $CH_3$ | $CH_2OCH_3$ | |
| 10 | $CH_3$ | 3-$NH_2$ | H | 6-$CH_3$ | $CH_3$ | $CH_3$ | $CH_2OCH_3$ | m.p. 117–118.5 |
| 11 | $CH_3$ | 4-$NH_2$ | 3-$CH_3$ | 6-$CH_3$ | $CH_3$ | $CH_3$ | $CH_2OCH_3$ | |
| 12 | $CH_3$ | 6-$NH_2$ | H | H | $CH_3$ | $CH_3$ | 2-furyl | |
| 13 | $CH_3$ | 6-$NH_2$ | H | H | $CH_3$ | $CH_3$ | 2-tetrahydrofuryl | |
| 14 | $CH_3$ | 3-$NH_2$ | H | 6-$CH_3$ | $CH_3$ | $CH_3$ | $CH_2SO_2CH_3$ | m.p. 106–110 |
| 15 | $CH_3$ | 6-$NH_2$ | H | H | $CH_3$ | $CH_3$ | $CH_2CH_2OCH_3$ | |

TABLE 1-continued

Compounds of formula I in which Ar = substituted phenyl, W = COOR$_8$, R$_5$ =H

| Compound | R$_1$ | R$_2$ | R$_3$ | R$_4$ | R | R$_8$ | B | Physical data [°C.] |
|---|---|---|---|---|---|---|---|---|
| 16 | CH$_3$ | 6-NH$_2$ | H | H | CH$_3$ | CH$_3$ | 1H—1,2,4-triazolyl-methyl | |
| 17 | CH$_3$ | 6-NH$_2$ | H | H | CH$_3$ | CH$_3$ | CH$_2$OCH$_2$CH=CH$_2$ | resin |
| 18 | CH$_3$ | 6-NH$_2$ | H | H | CH$_3$ | CH$_3$ | CH$_2$OCH$_2$C≡CH | resin |
| 19 | Cl | 6-NH$_2$ | 3-CH$_3$ | 4-CH$_3$ | CH$_3$ | C$_3$H$_7$—i | 2-furyl | |
| 20 | CH$_3$ | 4-NH$_2$ | 6-CH$_3$ | H | CH$_3$ | C$_3$H$_7$—i | CH$_2$SO$_2$CH$_3$ | |
| 21 | OCH$_3$ | 3-NH$_2$ | 6-CH$_3$ | H | CH$_3$ | CH$_3$ | 2-tetrahydrofuryl | |
| 22 | OCH$_3$ | 6-NH$_2$ | H | H | CH$_3$ | CH$_3$ | CH$_2$OCH$_3$ | |
| 23 | OCH$_3$ | 6-NH$_2$ | H | H | CH$_3$ | CH$_3$ | CH$_2$CH$_2$OCH$_3$ | |
| 24 | OCH$_3$ | 6-NH$_2$ | 3-Cl | H | CH$_3$ | CH$_3$ | 2-furyl | |
| 25 | OCH$_3$ | 3-NH$_2$ | 6-CH$_3$ | 4-CH$_3$ | CH$_3$ | CH$_3$ | CH$_2$OCH=CH$_2$ | |
| 26 | Cl | 3-NO$_2$ | 6-CH$_3$ | H | H | CH$_3$ | 2-tetrahydrofuryl | |
| 27 | Cl | 3-NO$_2$ | 6-CH$_3$ | H | CH$_3$ | CH$_3$ | CH$_2$OCH$_3$ | |
| 28 | CH$_3$ | 3-NO$_2$ | 6-CH$_3$ | H | CH$_3$ | CH$_3$ | CH$_2$OCH$_3$ | b.p. 170-174/0,07 mbar |
| 29 | CH$_3$ | 3-NO$_2$ | 6-CH$_3$ | 4-CH$_3$ | CH$_3$ | CH$_3$ | CH$_2$OCH$_3$ | m.p. 105-112° |
| 30 | CH$_3$ | 3-NO$_2$ | 6-CH$_3$ | H | H | CH$_3$ | CH$_2$OCH$_3$ | |
| 31 | CH$_3$ | 3-NO$_2$ | 6-CH$_3$ | H | CH$_3$ | CH$_3$ | CH$_2$OC$_2$H$_5$ | oil; n$_D^{24}$ = 1.5325 |
| 32 | C$_2$H$_5$ | 3-NO$_2$ | 6-CH$_3$ | H | CH$_3$ | CH$_3$ | CH$_2$OC$_2$H$_5$ | |
| 33 | CH$_3$ | 3-NO$_2$ | 6-CH$_3$ | H | CH$_3$ | C$_3$H$_7$—i | CH$_2$OCH$_3$ | oil |
| 34 | CH$_3$ | 3-NO$_2$ | 6-CH$_3$ | H | CH$_3$ | CH$_3$ | CH$_2$CH$_2$OCH$_3$ | |
| 35 | CH$_3$ | 3-NO$_2$ | 6-CH$_3$ | H | CH$_3$ | CH$_3$ | 2-tetrahydrofuryl | m.p. 97-104 |
| 36 | CH$_3$ | 3-NO$_2$ | 6-CH$_3$ | 4-CH$_3$ | CH$_3$ | C$_3$H$_7$—i | 2-furyl | |
| 37 | CH$_3$ | 3-NO$_2$ | 6-CH$_3$ | H | CH$_3$ | CH$_3$ | CH$_2$OSO$_2$CH$_3$ | |
| 38 | CH$_3$ | 3-NO$_2$ | 6-CH$_3$ | H | CH$_3$ | CH$_3$ | CH$_2$SO$_2$CH$_3$ | m.p. 168-172 |
| 39 | CH$_3$ | 3-NO$_2$ | 6-CH$_3$ | H | CH$_3$ | CH$_3$ | CH$_2$OCH$_2$CH=CH$_2$ | |
| 40 | OCH$_3$ | 3-NO$_2$ | 6-CH$_3$ | H | CH$_3$ | CH$_3$ | CH$_2$OCH$_2$C≡CH | semicrystalline |
| 41 | OC$_2$H$_5$ | 3-NO$_2$ | 6-CH$_3$ | H | CH$_3$ | CH$_3$ | CH$_2$SO$_2$CH$_3$ | |
| 42 | CH$_3$ | 3-NO$_2$ | 6-CH$_3$ | H | CH$_3$ | CH$_3$ | CH$_2$OSO$_2$NHC$_3$H$_7$—n | |
| 43 | CH$_3$ | 3-NO$_2$ | 6-CH$_3$ | H | CH$_3$ | CH$_3$ | CH$_2$OSO$_2$NHCH$_3$ | resin |
| 44 | CH$_3$ | 6-NO$_2$ | H | H | CH$_3$ | CH$_3$ | 2-furyl | |
| 45 | CH$_3$ | 6-NO$_2$ | H | H | CH$_3$ | CH$_3$ | 2-tetrahydrofuryl | |
| 46 | CH$_3$ | 6-NO$_2$ | H | H | CH$_3$ | CH$_3$ | CH$_2$CH$_2$OCH$_3$ | |
| 47 | CH$_3$ | 6-NO$_2$ | H | H | H | CH$_3$ | CH$_2$CH$_2$OCH$_3$ | |
| 48 | CH$_3$ | 6-NO$_2$ | H | H | CH$_3$ | CH$_3$ | CH$_2$OCH$_3$ | m.p. 59-61 |
| 49 | CH$_3$ | 6-NO$_2$ | H | H | CH$_3$ | CH$_3$ | CH$_2$OCH$_2$CH=CH$_2$ | resin |
| 50 | CH$_3$ | 6-NO$_2$ | H | H | CH$_3$ | CH$_3$ | CH$_2$OCHC≡CH | |
| 51 | CH$_3$ | 6-NO$_2$ | H | H | CH$_3$ | CH$_3$ | CH$_2$SO$_2$CH$_3$ | |
| 52 | CH$_3$ | 6-NO$_2$ | H | H | CH$_3$ | CH$_3$ | CH$_2$OSO$_2$CH$_3$ | |
| 53 | CH$_3$ | 6-NO$_2$ | H | H | CH$_3$ | CH$_3$ | CH$_2$OSO$_2$NH$_2$ | |
| 54 | CH$_3$ | 6-NO$_2$ | H | H | CH$_3$ | CH$_3$ | CH$_2$OSO$_2$NHC$_3$H$_7$—n | |
| 55 | CH$_3$ | 6-NO$_2$ | H | H | H | CH$_3$ | CH$_2$OCH$_3$ | |
| 56 | OCH$_3$ | 6-NO$_2$ | H | H | CH$_3$ | CH$_3$ | CH$_2$OCH$_3$ | |
| 57 | Cl | 6-NO$_2$ | H | H | CH$_3$ | CH$_3$ | CH$_2$OCH$_3$ | m.p. 95-99 |
| 58 | Br | 6-NO$_2$ | H | H | CH$_3$ | CH$_3$ | CH$_2$OCH$_3$ | |
| 59 | CH$_3$ | 6-NO$_2$ | 3-CH$_3$ | H | CH$_3$ | CH$_3$ | CH$_2$OCH$_3$ | m.p. 73-74 |
| 60 | CH$_3$ | 3-NO$_2$ | 6-CH$_3$ | H | CH$_3$ | CH$_3$ | 1H—1,2,4-triazolyl-methyl | m.p. 150-159 |
| 61 | CH$_3$ | 6-NO$_2$ | 3-CH$_3$ | 5-CH$_3$ | CH$_3$ | CH$_3$ | CH$_2$OCH$_3$ | |
| 62 | CH$_3$ | 6-NO$_2$ | 3-Cl | 5-CH$_3$ | CH$_3$ | CH$_3$ | CH$_2$OCH$_3$ | |
| 63 | CH$_3$ | 6-NO$_2$ | 4-Cl | 3-CH$_3$ | CH$_3$ | CH$_3$ | CH$_2$OCH$_3$ | |
| 64 | CH$_3$ | 6-NO$_2$ | 3-CH$_3$ | 4-CH$_3$ | CH$_3$ | CH$_3$ | CH$_2$OCH$_3$ | |
| 65 | OCH$_3$ | 6-NO$_2$ | 3-OCH$_3$ | H | CH$_3$ | CH$_3$ | CH$_2$OCH$_3$ | |
| 66 | OCH$_3$ | 6-NO$_2$ | 3-OCH$_3$ | H | CH$_3$ | C$_3$H$_7$—i | CH$_2$OCH$_3$ | |
| 67 | OCH$_3$ | 6-NO$_2$ | 3-OCH$_3$ | H | H | CH$_3$ | 2-furyl | |
| 68 | Cl | 6-NO$_2$ | 3-Cl | H | CH$_3$ | CH$_3$ | 2-furyl | resin |
| 69 | Cl | 6-NO$_2$ | 3-Cl | 4-CH$_3$ | CH$_3$ | CH$_3$ | 2-furyl | |
| 70 | Cl | 6-NO$_2$ | H | H | CH$_3$ | CH$_3$ | 1H—1,2,4-triazolyl-methyl | |
| 71 | Br | 6-NO$_2$ | 3-Br | H | CH$_3$ | CH$_3$ | CH$_2$OCH$_2$CH=CH$_2$ | |
| 72 | CH$_3$ | 6-NO$_2$ | 3-CH$_3$ | 4-CH$_3$ | CH$_3$ | C$_3$H$_7$—i | CH$_2$OC$_2$H$_5$ | |
| 73 | CH$_3$ | 3-NO$_2$ | 6-CH$_3$ | H | CH$_3$ | C$_3$H$_7$—i | CH$_2$OC$_2$H$_5$ | viscous oil |
| 74 | CH$_3$ | 3-NO$_2$ | 6-CH$_3$ | H | CH$_3$ | C$_2$H$_5$ | CH$_2$OCH$_3$ | red oil |
| 75 | CH$_3$ | 4-NO$_2$ | 6-CH$_3$ | H | CH$_3$ | CH$_3$ | CH$_3$OCH$_3$ | |
| 76 | Cl | 4-NO$_2$ | 6-Cl | H | CH$_3$ | CH$_3$ | CH$_3$OCH$_3$ | |
| 77 | OCH$_3$ | 4-NO$_2$ | 6-OCH$_3$ | H | CH$_3$ | CH$_3$ | CH$_3$OCH$_3$ | |
| 78 | CH$_3$ | 4-NO$_2$ | 6-CH$_3$ | 3-CH$_3$ | CH$_3$ | CH$_3$ | CH$_3$OCH$_3$ | m.p. 58-66 |
| 79 | CH$_3$ | 4-NO$_2$ | 6-CH$_3$ | H | CH$_3$ | CH$_3$ | 2-furyl | |
| 80 | CH$_3$ | 4-NO$_2$ | 6-CH$_3$ | H | CH$_3$ | CH$_3$ | 2-tetrahydrofuryl | |
| 81 | CH$_3$ | 4-NO$_2$ | 6-CH$_3$ | H | CH$_3$ | CH$_3$ | 1H—1,2,4-triazolyl-methyl | |
| 82 | CH$_3$ | 4-NO$_2$ | 6-CH$_3$ | H | CH$_3$ | CH$_3$ | CH$_2$OC$_2$H$_5$ | |
| 83 | CH$_3$ | 4-NO$_2$ | 6-CH$_3$ | H | CH$_3$ | CH$_3$ | CH$_2$CH$_2$OCH$_3$ | |
| 84 | CH$_3$ | 4-NO$_2$ | 6-CH$_3$ | H | CH$_3$ | C$_3$H$_7$—i | CH$_2$OCH$_3$ | |
| 85 | CH$_3$ | 4-NO$_2$ | 6-CH$_3$ | H | H | CH$_3$ | CH$_3$OCH$_3$ | |
| 86 | CH$_3$ | 4-NO$_2$ | 6-CH$_3$ | H | CH$_3$ | CH$_3$ | CH$_2$OCH$_2$CH=CH$_2$ | |
| 87 | CH$_3$ | 4-NO$_2$ | 6-CH$_3$ | H | CH$_3$ | CH$_3$ | CH$_2$OCH$_2$C≡CH | viscous; n$_D^{22}$ = 1.5532 |
| 88 | CH$_3$ | 3-NH$_2$ | 6-Cl | H | CH$_3$ | CH$_3$ | CH$_2$OC$_2$H$_5$ | |
| 89 | CH$_3$ | 4-NO$_2$ | 6-CH$_3$ | H | CH$_3$ | CH$_3$ | CH$_2$OSO$_2$CHC$_3$H$_7$—n | |
| 90 | CH$_3$ | 4-NO$_2$ | H | 6-CH$_3$ | CH$_3$ | CH$_3$ | CH$_2$OSO$_2$NHC$_3$H$_7$—n | |

TABLE 1-continued

Compounds of formula I in which Ar = substituted phenyl, W = COOR$_8$, R$_5$ = H

| Compound | R$_1$ | R$_2$ | R$_3$ | R$_4$ | R | R$_8$ | B | Physical data [°C.] |
|---|---|---|---|---|---|---|---|---|
| 91 | CH$_3$ | 6-NH$_2$ | 5-CH$_3$ | H | CH$_3$ | CH$_3$ | CH$_2$OCH$_3$ | |
| 92 | CH$_3$ | 3-NH$_2$ | 5-CH$_3$ | 6-CH$_3$ | CH$_3$ | CH$_3$ | CH$_2$CH$_2$OCH$_3$ | |
| 93 | CH$_3$ | 6-NH$_2$ | 5-CH$_3$ | H | CH$_3$ | CH$_3$ | 2-furyl | |
| 94 | CH$_3$ | 6-NO$_2$ | 5-CH$_3$ | H | CH$_3$ | CH$_3$ | CH$_2$OCH$_3$ | |
| 95 | CH$_3$ | 6-NO$_2$ | 5-CH$_3$ | H | CH$_3$ | CH$_3$ | 2-tetrahydrofuryl | |
| 96 | CH$_3$ | 6-NO$_2$ | 5-CH$_3$ | H | CH$_3$ | CH$_3$ | CH$_2$OCH$_2$CH=CH$_2$ | |
| 97 | CH$_3$ | 3-NO$_2$ | 5-CH$_3$ | 6-CH$_3$ | CH$_3$ | CH$_3$ | CH$_2$OCH$_3$ | |
| 98 | Cl | 3-NO$_2$ | 5-Cl | 6-CH$_3$ | CH$_3$ | CH$_3$ | CH$_2$OCH$_3$ | |
| 99 | Cl | 3-NO$_2$ | 6-Cl | 4-Cl | CH$_3$ | CH$_3$ | CH$_2$OCH$_3$ | |
| 100 | Cl | 6-NH$_2$ | 5-Cl | 4-Cl | CH$_3$ | CH$_3$ | 2-furyl | |
| 101 | CH$_3$ | 6-NH$_2$ | 5-CH$_3$ | 4-CH$_3$ | CH$_3$ | CH$_3$ | 1H—1,2,4-triazolyl-methyl | |
| 102 | CH$_3$ | 3-NO$_2$ | H | H | CH$_3$ | CH$_3$ | CH$_2$OCH$_3$ | m.p. 85-86 |
| 103 | CH$_3$ | 4-NO$_2$ | H | H | CH$_3$ | CH$_3$ | CH$_2$OCH$_3$ | m.p. 116-117 |
| 104 | CH$_3$ | 3-NO$_2$ | H | H | CH$_3$ | CH$_3$ | CH$_2$OC$_2$H$_5$ | yellowish oil |
| 105 | CH$_3$ | 3-NO$_2$ | H | H | CH$_3$ | C$_2$H$_5$ | CH$_2$OC$_2$H$_5$ | yellowish oil |
| 106 | F | 3-NO$_2$ | H | H | CH$_3$ | CH$_3$ | CH$_2$OCH$_3$ | m.p. 108-109 |
| 107 | CH$_3$ | 3-NO$_2$ | 6-Cl | H | CH$_3$ | CH$_3$ | CH$_2$OC$_2$H$_5$ | resin; n$_D^{30}$: 1.5336 |

TABLE 2

Compounds of formula I in which Ar = substituted phenyl, R$_5$ = H

| Compound | R$_1$ | R$_2$ | R$_3$ | R$_4$ | R | W | B | Physical data [°C.] |
|---|---|---|---|---|---|---|---|---|
| 108 | CH$_3$ | 3-NO$_2$ | 6-CH$_3$ | H | H | C(Cl)=CH$_2$ | CH$_2$OCH$_3$ | oil; n$_D^{25}$: 1.5596 |
| 109 | CH$_3$ | 3-NO$_2$ | H | H | H | C(Cl)=CH$_2$ | 2-Furyl | |
| 110 | CH$_3$ | 3-NO$_2$ | 6-CH$_3$ | H | CH$_3$ | C(Cl)=CH$_2$ | CH$_2$OC$_2$H$_5$ | |
| 111 | CH$_3$ | 3-NO$_2$ | 6-CH$_3$ | H | H | CH=CH$_2$ | CH$_2$OCH$_3$ | oil; n$_D^{28}$: 1.5500 |
| 112 | CH$_3$ | 3-NH$_2$ | 6-CH$_3$ | H | H | CH=CH$_2$ | CH$_2$OCH$_3$ | oil; n$_D^{25}$: 1.5695 |
| 113 | CH$_3$ | 3-NH$_2$ | 6-CH$_3$ | H | H | C(Cl)=CH$_2$ | CH$_2$OCH$_3$ | |
| 114 | CH$_3$ | 3-NH$_2$ | 6-CH$_3$ | H | H | C(Cl)=CCl$_2$ | CH$_2$OCH$_3$ | |
| 115 | CH$_3$ | 3-NH$_2$ | H | H | CH$_3$ | C(Cl)=CCl$_2$ | CH$_2$OCH$_3$ | |
| 116 | CH$_3$ | 3-NO$_2$ | H | H | H | C(Cl)=CCl$_2$ | CH$_2$OCH$_3$ | |
| 117 | CH$_3$ | 3-NO$_2$ | 6-CH$_3$ | H | H | C≡CH | CH$_2$OCH$_3$ | m.p. 63-64 |
| 118 | CH$_3$ | 3-NO$_2$ | H | H | H | C≡CH | CH$_2$OCH$_3$ | m.p. 69-73 |
| 119 | CH$_3$ | 3-NO$_2$ | H | H | CH$_3$ | C≡CH | CH$_2$SO$_2$CH$_3$ | |
| 120 | CH$_3$ | 3-NH$_2$ | 6-CH$_3$ | H | H | C≡CH | CH$_2$—OSO$_2$NHCH$_3$ | |
| 121 | CH$_3$ | 3-NO$_2$ | 6-CH$_3$ | H | H | C≡CH | CH$_2$OC$_2$H$_5$ | oil; n$_D^{20}$: 1.5568 |
| 122 | CH$_3$ | 3-NO$_2$ | 6-CH$_3$ | H | H | C≡CH | CH$_2$OC$_2$H$_5$ | m.p. 65-66 |
| 123 | CH$_3$ | 3-NO$_2$ | 6-CH$_3$ | H | CH$_3$ | COOCH$_3$ | CH=CH$_2$ | |
| 124 | CH$_3$ | 3-NO$_2$ | 6-CH$_3$ | H | CH$_3$ | COOCH$_3$ | cyclopropyl | |
| 125 | CH$_3$ | 3-NO$_2$ | 6-CH$_3$ | H | CH$_3$ | COOCH$_3$ | CH$_2$CH$_2$CH$_3$ | m.p. 145-147 |
| 126 | CH$_3$ | 3-NH$_2$ | 6-CH$_3$ | H | CH$_3$ | COOCH$_3$ | CH=CH$_2$ | |
| 127 | CH$_3$ | 3-NH$_2$ | 6-CH$_3$ | H | CH$_3$ | COOCH$_3$ | cyclopropyl | |
| 128 | CH$_3$ | 3-NH$_2$ | 6-CH$_3$ | H | CH$_3$ | COOCH$_3$ | CH$_2$CH$_2$CH$_3$ | |
| 129 | CH$_3$ | 3-NO$_2$ | 6-CH$_3$ | H | CH$_3$ | COOCH$_3$ | CH=CHCH$_3$ | m.p. 138-145 |
| 130 | CH$_3$ | 3-NH$_2$ | 6-CH$_3$ | H | CH$_3$ | COOCH$_3$ | CH=CHCH$_3$ | semicrystalline |
| 131 | CH$_3$ | 3-NO$_2$ | 6-Cl | H | CH$_3$ | COOCH$_3$ | CH$_2$CH$_2$CH$_3$ | m.p. 112-114 |
| 132 | CH$_3$ | 3-NO$_2$ | 6-CH$_3$ | H | CH$_3$ | COOCH$_3$ | cyclopropyl | m.p. 136-157 |
| 133 | CH$_3$ | 3-NO$_2$ | 6-CH$_3$ | 5-CH$_3$ | CH$_3$ | COOCH$_3$ | cyclopropyl | m.p. 90-107 |
| 134 | CH$_3$ | 3-NO$_2$ | 6-CH$_3$ | H | CH$_3$ | CN | CH$_2$OCH$_3$ | oil; n$_D^{25}$: 1.5589 |
| 135 | CH$_3$ | 3-NH$_2$ | 6-CH$_3$ | H | CH$_3$ | CN | CH$_2$OCH$_3$ | |
| 136 | CH$_3$ | 3-NO$_2$ | 6-CH$_3$ | 5-CH$_3$ | CH$_3$ | CN | CH$_2$OCH$_3$ | |
| 137 | CH$_3$ | 3-NH$_2$ | 6-CH$_3$ | 5-CH$_3$ | CH$_3$ | CN | CH$_2$OCH$_3$ | |
| 138 | Cl | 4-NO$_2$ | H | H | CH$_3$ | COOCH$_3$ | cyclopropyl | m.p. 138-143 |
| 139 | Cl | 4-NH$_2$ | H | H | CH$_3$ | COOCH$_3$ | cyclopropyl | m.p. 184-187 |
| 139a | CH$_3$ | 6-NO$_2$ | H | H | CH$_3$ | COOCH$_3$ | CH$_2$N(CH$_3$)$_2$ | |
| 139b | CH$_3$ | 6-NO$_2$ | H | H | CH$_3$ | COOCH$_3$ | CH$_2$N(C$_2$H$_5$)$_2$ | resin |
| 139c | CH$_3$ | 6-NO$_2$ | H | H | CH$_3$ | COOCH$_3$ | CH$_2$N(C$_3$H$_7$—n)$_2$ | |
| 139d | CH$_3$ | 6-NH$_2$ | H | H | CH$_3$ | COOCH$_3$ | CH$_2$N(CH$_3$)$_2$ | |
| 139e | CH$_3$ | 3-NO$_2$ | H | H | CH$_3$ | CN | CH$_2$N(C$_2$H$_5$)$_2$ | |

TABLE 3

Compounds of formula I in which Ar = substituted phenyl, R$_4$ = 5-CH$_3$, R$_5$ = 6-CH$_3$

| Compound | R$_1$ | R$_2$ | R$_3$ | R | R$_8$ | B | Physical data [°C.] |
|---|---|---|---|---|---|---|---|
| 140 | CH$_3$ | 4-NO$_2$ | 3-CH$_3$ | H | CH$_3$ | CH$_2$OCH$_3$ | |
| 141 | CH$_3$ | 4-NO$_2$ | 3-CH$_3$ | CH$_3$ | CH$_3$ | CH$_2$OCH$_3$ | m.p. 118-120 |
| 142 | CH$_3$ | 4-NO$_2$ | 3-CH$_3$ | CH$_3$ | CH$_3$ | CH$_2$OC$_2$H$_5$ | m.p. 124-128 |
| 143 | CH$_3$ | 4-NO$_2$ | 3-CH$_3$ | CH$_3$ | CH$_3$ | CH$_2$OC$_3$H$_7$—i | |
| 144 | CH$_3$ | 4-NO$_2$ | 3-CH$_3$ | CH$_3$ | CH$_3$ | 2-tetrahydrofuryl | m.p. 163-168 |
| 145 | CH$_3$ | 4-NO$_2$ | 3-CH$_3$ | CH$_3$ | CH$_3$ | 2-furyl | |
| 146 | CH$_3$ | 4-NO$_2$ | 3-CH$_3$ | CH$_3$ | CH$_3$ | CH$_2$OCH$_2$CH=CH$_2$ | |
| 147 | CH$_3$ | 4-NO$_2$ | 3-CH$_3$ | CH$_3$ | CH$_3$ | CH$_2$OCH$_2$C≡CH | |
| 148 | CH$_3$ | 4-NO$_2$ | 3-CH$_3$ | CH$_3$ | CH$_3$ | CH$_2$OSO$_2$NHCH$_3$ | |
| 149 | CH$_3$ | 4-NO$_2$ | 3-CH$_3$ | H | CH$_3$ | 2-furyl | |
| 150 | CH$_3$ | 4-NO$_2$ | 3-CH$_3$ | CH$_3$ | C$_2$H$_5$ | CH$_2$OCH$_3$ | |

TABLE 3-continued

Compounds of formula I in which Ar = substituted phenyl, $R_4$ = 5-$CH_3$, $R_5$ = 6-$CH_3$

| Compound | $R_1$ | $R_2$ | $R_3$ | R | $R_8$ | B | Physical data [°C.] |
|---|---|---|---|---|---|---|---|
| 151 | $CH_3$ | 4-$NO_2$ | 3-$CH_3$ | $CH_3$ | $C_2H_5$ | $CH_2OCH_3$ | |
| 152 | $CH_3$ | 4-$NO_2$ | 3-$CH_3$ | $CH_3$ | $C_3H_{7-i}$ | $CH_2OCH_3$ | |
| 153 | $CH_3$ | 4-$NO_2$ | 3-$CH_3$ | $CH_3$ | $C_3H_{7-n}$ | $CH_2OCH_3$ | |
| 154 | $C_2H_5$ | 4-$NO_2$ | 3-$CH_3$ | $CH_3$ | $CH_3$ | $CH_2OCH_3$ | |
| 155 | $CH_3$ | 4-$NO_2$ | 3-Cl | $CH_3$ | $CH_3$ | $CH_2OCH_3$ | |
| 156 | $CH_3$ | 4-$NO_2$ | 3-Cl | $CH_3$ | $CH_3$ | 2-furyl | |
| 157 | $CH_3$ | 4-$NH_2$ | 3-$CH_3$ | H | $CH_3$ | $CH_2OCH_3$ | |
| 158 | $CH_3$ | 4-$NH_2$ | 3-$CH_3$ | $CH_3$ | $CH_3$ | $CH_2OCH_3$ | m.p. 120.5–123 |
| 159 | $CH_3$ | 4-$NH_2$ | 3-$CH_3$ | $CH_3$ | $CH_3$ | $CH_2OC_2H_5$ | m.p. 75.5–82 |
| 160 | $CH_3$ | 4-$NH_2$ | 3-$CH_3$ | $CH_3$ | $CH_3$ | $CH_2OC_3H_{7-i}$ | |
| 161 | $CH_3$ | 4-$NH_2$ | 3-$CH_3$ | $CH_3$ | $CH_3$ | 2-tetrahydrofuryl | m.p. 156–161 |
| 162 | $CH_3$ | 4-$NH_2$ | 3-$CH_3$ | $CH_3$ | $CH_3$ | 2-furyl | |
| 163 | $CH_3$ | 4-$NH_2$ | 3-$CH_3$ | $CH_3$ | $CH_3$ | $CH_2OCH_2CH=CH_2$ | |
| 164 | $CH_3$ | 4-$NH_2$ | 3-$CH_3$ | $CH_3$ | $CH_3$ | $CH_2OCH_2C\equiv CH$ | |
| 165 | $CH_3$ | 4-$NH_2$ | 3-$CH_3$ | $CH_3$ | $CH_3$ | $CH_2OSO_2NHCH_3$ | |

TABLE 4

Compounds of formula I in which Ar = α-naphthyl, $R_2$ = 2-$NO_2$

| Compound | $R_3$ | $R_6$ | R | W | B | Physical data [°C.] |
|---|---|---|---|---|---|---|
| 400 | H | H | $CH_3$ | $COOCH_3$ | $CH_2OCH_3$ | m.p. 103–107 |
| 401 | H | H | H | $COOCH_3$ | $CH_2OCH_3$ | |
| 402 | $CH_3$ | H | $CH_3$ | $COOCH_3$ | $CH_2OCH_3$ | viscous resin |
| 403 | H | H | $CH_3$ | $COOCH_3$ | $CH_2OC_2H_5$ | |
| 404 | H | H | H | $COOCH_3$ | 2-furyl | |
| 405 | H | H | H | $COOCH_3$ | 2-tetrahydrofuryl | |
| 406 | H | H | $CH_3$ | $COOCH_3$ | $CH_2SO_2CH_3$ | |
| 407 | H | H | H | $COOCH_3$ | $CH_2CH_2OCH_3$ | |
| 408 | H | H | $CH_3$ | $COOCH_3$ | $CH_2OCH_2CH=CH_2$ | viscous resin |
| 409 | H | H | $CH_3$ | $COOCH_3$ | $CH_2OCH_2C\equiv CH$ | semicrystalline |
| 410 | H | H | $CH_3$ | $COOCH_3$ | 1H—1,2,4-triazolyl-methyl | |
| 411 | H | H | $CH_3$ | $COOCH_3$ | $CH_2OSO_2CH_3$ | |
| 412 | H | H | H | $COOCH_3$ | $CH_2OSO_2NHCH_3$ | |
| 413 | H | H | $CH_3$ | $COOCH_3$ | $CH_2OSO_2NHCH_3$ | |
| 414 | H | H | H | $C\equiv CH$ | $CH_2OCH_3$ | |
| 415 | H | H | H | $C\equiv CH$ | $CH_2OC_2H_5$ | |
| 416 | H | H | $CH_3$ | $C\equiv CH$ | $CH_2OCH_3$ | |
| 417 | H | H | H | CN | $CH_2OCH_3$ | |
| 418 | H | H | $CH_3$ | CN | $CH_2OCH_3$ | |
| 419 | H | H | $CH_3$ | $CH=CH_2$ | $CH_2OCH_3$ | viscous oil |
| 420 | H | H | $CH_3$ | $C(Cl)=CCl_2$ | $CH_2OCH_3$ | |
| 421 | 5-Br | H | H | $COOCH_3$ | $CH_2OCH_3$ | |
| 422 | 5-Br | H | $CH_3$ | $COOC_2H_5$ | $CH_2OCH_3$ | |
| 423 | 5-Br | H | $CH_3$ | $COOCH_3$ | $CH_2OCH_3$ | |
| 424 | 5-Br | 4-$CH_3$ | $CH_3$ | $C\equiv CH$ | 2-furyl | |
| 425 | 5-Br | H | $CH_3$ | CN | 2-tetrahydrofuryl | resin |
| 426 | 5-Br | H | $CH_3$ | $CH=CH_2$ | $CH_2OCH_3$ | |
| 427 | 5-Br | H | $CH_3$ | $C(Cl)=CCl_2$ | $CH_2OCH_3$ | |
| 428 | 5-Br | H | $CH_3$ | $COOCH_3$ | cyclopropyl | |
| 429 | H | H | $CH_3$ | $COOCH_3$ | cyclopropyl | |
| 430 | H | 4-$CH_3$ | $CH_3$ | $COOCH_3$ | $CH_2OCH_3$ | |

TABLE 5

Compounds of formula I in which Ar = α-naphthyl, $R_2$ = 5-$NO_2$

| Compound | $R_3$ | $R_6$ | R | W | B | Physical data [°C.] |
|---|---|---|---|---|---|---|
| 501 | 2-$CH_3$ | H | H | $COOCH_3$ | $CH_2OCH_3$ | |
| 502 | 2-$CH_3$ | H | $CH_3$ | $COOCH_3$ | $CH_2OCH_3$ | |
| 503 | 2-$CH_3$ | H | $CH_3$ | $COOC_2H_5$ | $CH_2OCH_3$ | |
| 504 | 2-$CH_3$ | H | $CH_3$ | $C\equiv CH$ | $CH_2OCH_3$ | |
| 505 | 2-$CH_3$ | H | $CH_3$ | $C\equiv CCl$ | $CH_2OCH_3$ | resin |
| 506 | 2-$CH_3$ | H | $CH_3$ | $CH=CH_2$ | $CH_2OCH_3$ | |
| 507 | 2-$CH_3$ | H | H | $C(Cl)=CH_2$ | $CH_2OCH_3$ | |
| 508 | 2-$CH_3$ | H | $CH_3$ | CN | $CH_2OCH_3$ | |
| 509 | 2-$CH_3$ | H | $CH_3$ | $COOCH_3$ | $CH_2OSO_2NHCH_3$ | |
| 510 | 2-$CH_3$ | H | $CH_3$ | $COOCH_3$ | $CH_2CH_2OCH_3$ | |
| 511 | 2-$CH_3$ | H | $CH_3$ | $COOCH_3$ | $CH_2SO_2CH_3$ | |
| 512 | 2-$CH_3$ | H | $CH_3$ | $COOCH_3$ | $CH_2OCH_2C\equiv CH$ | resin |
| 513 | 2-$CH_3$ | 3-$CH_3$ | $CH_3$ | $CH=CH_2$ | $CH_2OCH_3$ | |
| 514 | 2-$CH_3$ | 3-$CH_3$ | H | $CH=CH_2$ | $CH_2OCH_3$ | |
| 516 | 2-$CH_3$ | H | H | $COOCH_3$ | $CH_2N(CH_3)_2$ | |

TABLE 6

Compounds of formula I in which Ar = α-naphthyl, $R_2$ = 4-$NO_2$

| Compound | $R_3$ | $R_6$ | R | W | B | Physical data [°C.] |
|---|---|---|---|---|---|---|
| 601 | 2-$CH_3$ | 3-$CH_3$ | H | $COOCH_3$ | $CH_2OCH_3$ | |
| 602 | 2-$CH_3$ | 3-$CH_3$ | $CH_3$ | $COOCH_3$ | $CH_2OCH_3$ | |
| 603 | 2-$CH_3$ | 3-$CH_2$ | $CH_3$ | $COOC_2H_5$ | $CH_2OCH_3$ | |
| 604 | 2-$CH_3$ | 3-$CH_3$ | $CH_3$ | CN | 2-furyl | |
| 605 | 2-$CH_3$ | 3-$CH_3$ | $CH_3$ | $COOCH_3$ | $CH_2SO_2CH_3$ | |
| 606 | 2-$CH_3$ | H | $CH_3$ | $COOCH_3$ | $CH_2OCH_3$ | m.p. 93.5–99 |
| 607 | 2-$CH_3$ | H | $CH_3$ | $COOCH_3$ | 2-tetrahydrofuryl | viscous; $n_D^{21}$ 1.5948 |
| 608 | 2-$CH_3$ | H | H | C≡CH | $CH_2OCH_3$ | |
| 609 | H | H | $CH_3$ | $COOC_2H_5$ | $CH_2OCH_3$ | m.p. 103–105 |
| 610 | J | H | H | $COOCH_3$ | $CH_2OCH_3$ | |
| 611 | H | H | $CH_3$ | $COOCH_3$ | $CH_2OCH_3$ | m.p. 110–116 |
| 612 | H | H | $CH_3$ | $COOCH_3$ | 1H—1,2,4-triazolyl-methyl | |
| 613 | 2-$CH_3$ | 3-$CH_3$ | $CH_3$ | $COOCH_3$ | 1H—1,2,4-triazolyl-methyl | |
| 614 | 2-$CH_3$ | 3-$CH_3$ | H | CH=$CH_2$ | $CH_2OCH_3$ | |
| 615 | H | H | H | C≡CH | $CH_2OCH_3$ | m.p. 111–114 |

TABLE 7

Compounds of formula I in which Ar = α-naphthyl $R_2$ = 2-$NH_2$

| Compound | $R_3$ | $R_6$ | R | W | B | Physical data [°C.] |
|---|---|---|---|---|---|---|
| 701 | H | H | $CH_3$ | $COOCH_3$ | $CH_2OCH_3$ | m.p. 159–162 |
| 702 | H | H | H | $COOCH_3$ | $CH_2OCH_3$ | |
| 703 | H | H | $CH_3$ | $COOCH_3$ | 2-tetrahydrofuryl | |
| 704 | H | H | $CH_3$ | $COOCH_3$ | 2-furyl | |
| 705 | H | H | $CH_3$ | $COOCH_3$ | $CH_2SO_2CH_3$ | |
| 706 | H | H | $CH_3$ | $COOCH_3$ | $CH_2OSO_2CH_3$ | |
| 707 | H | H | H | C≡CH | $CH_2OCH_3$ | |
| 708 | H | H | H | CH=$CH_2$ | $CH_2CH_2CH$=$CH_2$ | |
| 709 | H | H | H | C(Cl)=$CCl_2$ | $CH_2OCH_3$ | |
| 710 | 5-Br | H | $CH_3$ | $COOCH_3$ | $CH_2OCH_3$ | |
| 711 | 5-Br | H | $CH_3$ | $COOC_2H_5$ | $CH_2OCH_3$ | |
| 712 | 5-Br | H | $CH_3$ | $COOCH_3$ | 2-furyl | resin |
| 713 | H | 5-$CH_3$ | $CH_3$ | $COOCH_3$ | $CH_2OCH_3$ | |
| 714 | H | H | $CH_3$ | $COOCH_3$ | $CH_2OSO_2NHCH_3$ | |
| 715 | H | H | $CH_3$ | $COOCH_3$ | $CH_2N(CH_3)_2$ | |

TABLE 8

Compounds of formula I in which Ar = α-naphthyl

| Compound | $R_2$ | $R_3$ | $R_6$ | R | W | B | phys. data |
|---|---|---|---|---|---|---|---|
| 801 | 4-$NH_2$ | H | H | H | $COOCH_3$ | $CH_2OCH_3$ | |
| 802 | 4-$NH_2$ | H | H | $CH_3$ | $COOCH_3$ | $CH_2OCH_3$ | |
| 803 | 4-$NH_2$ | H | H | H | CH=$CH_2$ | $CH_2OCH_3$ | |
| 804 | 4-$NH_2$ | H | H | $CH_3$ | $COOC_2H_5$ | | |
| 805 | 4-$NH_2$ | H | H | H | C≡CH | $CH_2OSO_2CH_3$ | |
| 806 | 4-$NH_2$ | 2-$CH_3$ | H | $CH_3$ | $COOCH_3$ | $CH_2OCH_3$ | m.p. 161–167 |
| 807 | 4-$NH_2$ | 2-$CH_3$ | H | $CH_3$ | CN | $CH_2OCH_3$ | |
| 808 | 4-$NH_2$ | 2-$CH_3$ | 3-$CH_3$ | $CH_3$ | $COOCH_3$ | $CH_2OCH_3$ | |
| 809 | 4-$NH_2$ | 2-$CH_3$ | H | $CH_3$ | $COOCH_3$ | 2-tetrahydrofuryl | m.p. 206–220 |
| 810 | 5-$NH_2$ | 2-$CH_3$ | H | H | $COOCH_3$ | $CH_2OCH_3$ | |
| 811 | 5-$NH_2$ | 2-$CH_3$ | H | $CH_3$ | $COOCH_3$ | $CH_2OCH_3$ | |
| 812 | 5-$NH_2$ | 2-$CH_3$ | H | H | C≡CH | $CH_2OCH_3$ | |
| 813 | 5-$NH_2$ | 2-$CH_3$ | H | H | C(Cl)=$CCl_2$ | $CH_2OCH_3$ | |
| 814 | 5-$NH_2$ | 2-$CH_3$ | H | $CH_3$ | $COOCH_3$ | 2-furyl | |
| 815 | 4-$NH_2$ | H | H | H | $COOCH_3$ | $CH_2OSO_2NHCH_3$ | |
| 816 | 4-$NH_2$ | H | H | $CH_3$ | $COOCH_3$ | $CH_2N(CH_3)_2$ | |

For application, the compounds of the formula I can be processed to the following formulations:

FORMULATION EXAMPLES

EXAMPLE 7

Solid formulations: Dusts and tracking powders contain in general up to 10% of active ingredient. A 5% dust can consist for example of 5 parts of active ingredient and 95 parts of an adjuvant, such as talcum; and a 2% dust of 2 parts of active ingredient, 1 part of highly dispersed silica and 97 parts of talcum. Further mixtures with these and other carriers and adjuvants commonly employed in the art of formulation are also possible.

These dusts and tracking powders are produced by mixing and grinding the active ingredients with the carriers and adjuvants, and can be applied in this form by dusting.

Granulates, such as coated, impregnated and homogeneous granulates and also pellets, usually contain 1 to 80% of active ingredient. A 5% granulate can thus be composed of e.g. 5 parts of active ingredient, 0.25 part of epoxidised vegetable oil, 0.25 part of cetyl polyglycol ether, 3.50 parts of polyethylene glycol and 91 parts of kaolin (preferred particle size 0.3–0.8 mm). The granulate can be prepared as follows: The active ingredient is mixed with the vegetable oil, the mixture is dissolved in 6 parts of acetone, and the polyethylene glycol and cetyl polyglycol ether are added. The solution obtained is sprayed onto kaolin, and the acetone is subsequently evaporated off in vacuo. A microgranulate of this type is advantageously used for controlling soil fungi.

EXAMPLE 8

Liquid formulations: A distinction is generally made between active ingredient concentrates which are dispersible or soluble in water, and aerosols. Active ingredient concentrates dispersible in water include e.g. wettable powders and pastes, which usually contain 25–90% of active ingredient in commercial packs, and 0.01 to 15% of active ingredient in ready-for-use solutions. Emulsifiable concentrates contain 10 to 50% of active ingredient, and solution concentrates contain in ready-for-use solution 0.001 to 20% of active ingredient. A 70% wettable powder can thus be composed of e.g. 70 parts of active ingredient, 5 parts of sodium dibutylnaphthalenesulfonate, 3 parts of naphthalenesulfonic acid/phenolsulfonic acid/formaldehyde condensate (in the ratio of 3:2:1), 10 parts of kaolin and 12 parts of chalk, for example Champagne chalk. A 40% wettable powder can consist e.g. of the following substances: 40 parts of active ingredient, 5 parts of sodium lignosulfonate, 1 part of sodium dibutylnaphthalenesulfonate and 54 parts of silicic acid. A 25% wettable powder can be formulated in different ways. It can be composed e.g. of: 25 parts of active ingredient, 4.5 parts of calcium lignosulfonate, 1.9 parts of chalk, for example a mixture of Champagne chalk/hydroxyethylene cellulose (1:1), 1.5 parts of sodium dibutylnaphthalenesulfonate, 19.5 parts of silicic acid, 19.5 parts of Champagne chalk and 28.1 parts of kaolin. A 25% wettable powder can also consist of e.g.: 25 parts of active ingredient, 2.5 parts of isooctylphenoxy-polyoxyethylene-ethanol, 1.7 parts of a mixture of Champagne chalk/hydroxyethyl cellulose (1:1), 8.3 parts of sodium silicate, 16.5 parts of kieselguhr and 46 parts of kaolin. A 10% wettable powder can be formulated e.g. from: 10 parts of active ingredient, 3 parts of a mixture of the sodium salt of saturated fatty alcohol sulfonates, 5 parts of naphthalenesulfonic acid/formaldehyde condensate and 82 parts of kaolin. Other wettable powders can be formulated as mixtures of 5 to 30% of active ingredient together with 5 parts of an adsorbent carrier material, such as silicic acid, 55 to 80 parts of a carrier such as kaolin, and a dispersing agent mixture consisting of 5 parts of sodium arylsulfonate and 5 parts of an alkylaryl polyglycol ether. A 25% emulsifiable concentrate can contain e.g. the following emulsifiable substances: 25 parts of active ingredient, 2.5 parts of epoxidised vegetable oil, 10 parts of a mixture of an alkylarylsulfonate and a fatty alcohol polyglycol ether, 5 parts of dimethyl formamide and 57.5 parts of xylene. Emulsions of the desired concentration can be prepared from such concentrates by dilution with water. These emulsions are particularly suitable for leaf application. It is, moreover, possible to produce further wettable powders having other mixture ratios and containing other carriers and adjuvants customarily employed in formulation technology. The active ingredients are intimately mixed in suitable mixers with the stated adjuvants, and subsequently ground on the appropriate mills and rollers. Wettable powders having excellent wetting and suspension properties are obtained: These wettable powders can be diluted with water to obtain suspensions of the desired concentration, and are particularly suitable for leaf application. The invention also relates to such compositions.

Compositions formulated as described above and which contain, as active ingredient, a compound of the formula I (for example compounds 2, 6, 8, 10, 28, 31, 33, 48, 57, 59, 73 or 74) can be used very successfully for controlling phytopathogenic microorganisms. Other compounds of Tables 1 to 8 can also be used with equally good or similar success.

BIOLOGICAL EXAMPLES

EXAMPLE 9

Action Against *Erysiphe graminis* on Barley

Residual protective action

Barley plants about 8 cm in height are sprayed with a spray mixture (0.02% of active ingredient) prepared from the active ingredient formulated as a wettable powder. The treated plants are dusted with conidia of the fungus after 3–4 hours. The infected barley plants are then stood in a greenhouse at about 22° C. The extent of the fungus infection is evaluated after 10 days.

In the treatment of barley plants against Erysiphe fungi with compounds of the formula I, e.g. compounds 10, 38, 60, 104, 107 or 142, the fungus attack was reduced to less than 10% compared with control plants (100% attack).

EXAMPLE 10

Action Against *Phytophthora infestans* on Tomato Plants (a) Residual-protective action Tomato plants are sprayed, after 3-weeks' cultivation, with a spray mixture prepared from the active ingredient formulated as a wettable powder (0.06% of active ingredient). After 24 hours, the treated plants are infested with a suspension of sporangia of the fungus. Evaluation of the fungus attack is made after incubation of the infested plants for 5 days at 20° C. and 90°–100° C. relative humidity. Compared with untreated control plants (100% attack), plants treated with one of compounds 2, 6, 8, 10, 14, 28, 29, 31, 33, 35, 38, 48, 57, 59, 60, 73, 74, 78, 88, 102 to 107, 111, 117, 122, 138, 139, 141, 142, 144, 158, 159, 161, 400, 606, 607, 611 or 701, exhibit less than 10% attack.

(b) Systemic action

A spray mixture prepared from the active ingredient formulated as a wettable powder (0.06% of active ingredient, based on the volume of soil) is applied to tomato plants which have been cultivated for 3 week. Care is taken to ensure that the spray mixture does not come in contact with the parts of the plants above the soil. After 48 hours, the treated plants are infested with a suspension of sporangia of the fungus. Evaluation of fungus attack is made after incubation of the infested plants for 5 days at 20° C. and 90–100% relative humidity.

In this test, compounds 2, 6, 8, 10, 14, 28, 29, 31, 33, 35, 38, 48, 57, 59, 60, 73, 74, 78, 88, 102 to 107, 111, 117, 122, 138, 139, 141, 142, 144, 158, 159, 161, 400, 606, 607, 611 and 701 among others, exhibit a very good systemic action. Compared with untreated control plants (100% attack), fungus attack is almost completely inhibited (0 to 5%) with these compounds.

(c) Residual curative action

After a cultivation period of three weeks, tomato plants are infested with a suspension of sporangia of the fungus. After an incubation time of 22 hours in a humid chamber at 20° C. and 90-100% relative humidity, the infested plants are dried, and subsequently sprayed with a spray mixture prepared from the active ingredient formulated as wettable powder (0.6% of active ingredient). After the coating has dried, the treated plants are returned to the humid chamber. Evaluation of fungus attack is made 5 days after infestation.

Compared with untreated and infected control plants (100% attack), plants treated with one of compounds 2, 6, 8, 10, 28, 29, 31, 33, 48, 59, 74, 107, 141, 142, 161, 400, 606, 611 and 701 exhibit less than 10% attack.

EXAMPLE 11

Residual-protective Action Against *Venturia inaequalis* on Apple Shoots

Apple cuttings with 10-20 cm long fresh shoots are sprayed with a spray mixture prepared from a wettable powder formulation of the active ingredient (0.06%). After 24 hours the treated plants are infected with a conidia suspension of the fungus. The plants are then incubated for 5 days at 90-100% relative humidity and stood in a greenhouse for a further 10 days at 20°-24° C. Scab infestation is evaluated 15 days after infection.

Anong others, compounds 8, 10, 28, 31 and 701 reduced infestation to 10-15%.

EXAMPLE 12

Action on *Pythium debaryanum* on Sugar Beets (a) Action after soil application

The fungus is cultivated on carrot chips nutrient solution and added to a mixture of earth and sand. Flower pots are filled with the infected soil, in which sugar beet seeds are then sown. Immediately after sowing, the test preparations formulated as wettable powders are poured in the form of aqueous suspensions over the soil (20 ppm of active ingredient, based on the volume of the soil). The pots are then stood for 2-3 weeks in a greenhouse at 20°-24° C. The soil is kept uniformly moist by gently spraying it with water. The emergence of the sugar beet plants as well as the number of healthy and sick plants are ascertained in evaluating the test.

(b) Action after seed dressing application

The fungus is cultivated on carrot chip nutrient solution and added to a mixture of earth and sand. Flower pots are filled with the infected soil and sugar beet seeds which have been treated with the test preparations formulated as seed dressing powders are sown therein (0.06% of one of the compounds of Tables 1 and 2). The pots are then stood in a greenhouse for 2-3 weeks at c. 20° C. The soil is kept uniformly moist by gently spraying it with water. The emergence of the sugar beet plants is ascertained in evaluating the test.

In both tests, compounds 2, 6, 8, 10, 28, 29, 31, 33, 48, 59, 73, 107, 158, 160, 400, 606, 607 and 701 are fully effective against *Pythium pathogens* (over 90% emergent plants). The plants have a healthy appearance.

An equally good action is achieved in analogous tests against *Pythium pathogens* on maize.

EXAMPLE 13

Residual-protective Action Against *Podosphaera leucotricha* on Apples

Apple seedlings in the 5-leaf stage are sprayed with a spray mixture (0.06% of active ingredient) prepared from a wettable powder formulation of the active ingredient. After 24 hours the treated plants are infected with a conidia suspension of the fungus and placed in a climatic chamber at 70% relative humidity and 20° C. Evaluation of fungus infestation is made 12 days after infection.

Compared with untreated and infected control seedlings (100% attack) seedlings treated with one of compounds 2, 6, 8, 10, 28, 31, 33, 48, 73 or 606 exhibit less than 10% attack.

EXAMPLE 14

Determination of Physico-chemical Data

Compared with the commercially available fungicide "Metalaxyl" (N-(2,6-dimethylphenyl)-N-(2'-methoxyacetyl)alanine methyl ester) known from U.S. Pat. No. 4,151,299, the compounds of this invention, which have a similar chemical structure, have physico-chemical data which are markedly more advantageous for the residual action of a fungicide.

(a) Reduced water solubility

| Compound | Solubility at 25° C. |
|---|---|
| Metalaxyl | 800 ppm |
| 48 | 4000 ppm |
| 28 | 2500 ppm |
| 31 | 2500 ppm |
| 33 | 500 ppm |
| 2 | 300 ppm |

(b) Reduced volatility

In an evaporating tube, the evaporation half-life values $T_{50}$ of representative fungicides of this invention are determined at 50° C. and in a stream of air of 20 m/h. The values are shown below, relative to the corresponding half-life $T_{50}$ of Metalaxyl.

| Compound | Multiple of Metalaxyl $T_{50}$ |
|---|---|
| 2 | 5.4 × |
| 48 | 12.3 × |
| 28 | 35.8 × |
| 31 | 41.8 × |
| 33 | 45.6 × |

The above tests (a) and (b) demonstrate the physico-chemical advantages of the compounds of the formula I. These advantages prevent an unwanted premature loss of active ingredient and thereby ensure a longer lasting effect of the compositions.

What is claimed is:

1. A compound of the formula

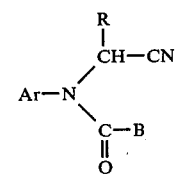

wherein
R is hydrogen or methyl,
Ar is one of the aromatic groups

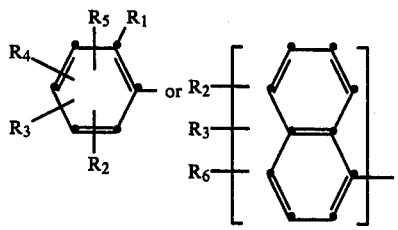

wherein $R_1$ is $C_1$-$C_3$alkyl, $C_1$-$C_3$alkoxy or halogen,
$R_2$ is $NO_2$ or $NH_2$,
$R_3$ is hydrogen, $C_1$-$C_3$alkyl, $C_1$-$C_3$alkoxy or halogen,
$R_4$ is hydrogen or $C_1$-$C_3$alkyl,
$R_5$ is hydrogen or $C_1$-$C_3$alkyl, and
$R_6$ is hydrogen, $C_1$-$C_3$alkyl or halogen;
B is $C_3$-$C_4$alkyl, $C_2$-$C_4$alkenyl, cyclopropyl, 2-furyl, 2-tetrahydrofuryl, $\beta$-($C_1$-$C_2$alkoxy)ethyl or the group $CH_2Z$, in which Z is 1H-1,2,4-triazolyl, methylsulfonyl, X—$R_{13}$, $OSO_2$—$R_{14}$ or —$N(R_{15})(R_{16})$, in which X is oxygen or sulfur, $R_{13}$ is an alkyl, alkenyl or alkynyl group, each containing at most 4 carbon atoms.

$R_{14}$ is $C_1$-$C_3$alkyl or $NH(C_1$-$C_3$alkyl), and $R_{15}$ and $R_{16}$, each independently of the other, are $C_1$-$C_3$alkyl.

2. A compound according to claim 1, wherein $R_1$ is methyl, ethyl, methoxy, ethoxy or halogen; each of $R_3$ and $R_6$ independently is hydrogen, methyl, ethyl, methoxy, ethoxy or halogen; each of $R_4$ and $R_5$ independently is hydrogen, methyl or ethyl; and B is $C_1$-$C_3$alkyl, $C_2$-$C_4$alkenyl, cyclopropyl, 2-furyl, 2-tetrahydrofuryl, $CH_2O(C_1$-$C_3$alkyl), 1H-1,2,4-triazolylmethyl, $CH_2SO_2CH_3$, $CH_2OSO_2CH_3$, $CH_2OCH_2CH$=$CH_2$, $CH_2OCH_2C$≡$CH$, $CH_2OSO_2NHCH_3$, $CH_2N(CH_3)_2$, $CH_2N(C_2H_5)_2$ or $CH_2N(C_3H_7$-n$)_2$.

3. A compound according to claim 2, wherein R is methyl; $R_1$ is methyl, methoxy, chlorine or bromine; each of $R_3$ and $R_6$ independently is hydrogen, methyl, chlorine or bromine; each of $R_4$ and $R_5$ independently is hydrogen or methyl; and B is 2-furyl, 2-tetrahydrofuryl, $CH_2O(C_1$-$C_3$alkyl), 1H-1,2,4-triazolylmethyl, $CH_2SO_2CH_3$, $CH_2OSO_2CH_3$, $CH_2OCH_2CH$=$CH_2$, $CH_2OCH_2C$≡$CH$, $CH_2OSO_2NHCH_3$, $CH_2N(CH_3)_2$, $CH_2N(C_2H_5)_2$ or $CH_2N(C_3H_7$-n$)_2$.

4. A composition for controlling and/or preventing attack by harmful microorganisms, which composition contains a compound according to claim 1 and a carrier.

5. A composition according to claim 4, which contains 0.01 to 90% by weight of the compound, 10 to 99.99% by weight of adjuvants, and 0 to 33% b weight of a surfactant.

6. A method of controlling and/or protecting plants from attack by phytopathogenic microorganisms, which method comprises applying to said plants or to the locus thereof a microbicidally effective amount of a compound according to claim 1.

7. A method according to claim 6, wherein the microorganisms to be controlled are phytopathogenic fungi.

8. A method according to claim 6 in which, in the compound, $R_1$ is methyl, ethyl, methoxy, ethoxy or halogen,
each of $R_3$ and $R_6$ independently is hydrogen, methyl, ethyl, methoxy, ethoxy or halogen,
each of $R_4$ and $R_5$ independently is hydrogen, methyl or ethyl, and
B is $C_1$-$C_3$alkyl, $C_2$-$C_4$-alkenyl, cyclopropyl, 2-furyl, 2-tetrahydrofuryl, $CH_2O(C_1$-$C_3$alkyl), 1H-1,2,4-triazolylmethyl, $CH_2SO_2CH_3$, $CH_2OSO_2CH_3$, $CH_2OCH_2CH$=$CH_2$, $CH_2OCH_2C$≡$C$, $CH_2OSO_2NHCH_3$, $CH_2N(CH_3)_2$, $CH_2N(C_2H_5)_2$ or $CH_2N(C_3H_7$-n$)_2$.

9. A method according to claim 8 in which
R is methyl,
$R_1$ is methyl, methoxy, chlorine or bromine,
each of $R_3$ and $R_6$ independently is hydrogen, methyl, chlorine or bromine,
each or $R_4$ and $R_5$ independently is hydrogen or methyl, and
B is 2-furyl, 2-tetrahydrofuryl, $CH_2O(C_1$-$C_3$alkyl), 1H-1,2,4-triazolylmethyl, $CH_2SO_2CH_3$, $CH_2OSO_2CH_3$, $CH_2OCH_2CH$=$CH_2$, $CH_2OCH_2C$≡$C$, $CH_2OSO_2NHCH_3$, $CH_2N(CH_3)_2$, $CH_2N(C_2H_5)_2$ or $CH_2N(C_3H_7$-n$)_2$.

* * * * *

UNITED STATES PATENT AND TRADEMARK OFFICE
CERTIFICATE OF CORRECTION

PATENT NO. : 4,438,125
DATED : March 20, 1984
INVENTOR(S) : Adolf Hubele, Wolfgang Eckhardt, and Peter Riebli It is certified that error appears in the above-identified patent and that said Letters Patent is hereby corrected as shown below:

Claim 5, Column 30, Line 9 should read--

99.99% by weight of adjuvants, and 0 to 33% by weight --.

Claim 9, Column 30, Line 42 should read--

$SO_2CH_3$, $CH_2OCH_2CH=CH_2$, $CH_2OCH_2C{\equiv}CH$, --.

Signed and Sealed this

First Day of October 1985

[SEAL]

Attest:

Attesting Officer

DONALD J. QUIGG

Commissioner of Patents and Trademarks—Designate